US010226523B2

(12) United States Patent
Lanis et al.

(10) Patent No.: US 10,226,523 B2
(45) Date of Patent: Mar. 12, 2019

(54) CLOSTRIDIUM DIFFICILE VACCINE AND METHODS OF USE

(71) Applicant: Board of Regents of the University of Oklahoma, Norman, OK (US)

(72) Inventors: Jordi M. Lanis, Norman, OK (US); Jimmy D. Ballard, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 49 days.

(21) Appl. No.: 14/786,415

(22) PCT Filed: Apr. 22, 2014

(86) PCT No.: PCT/US2014/035029
§ 371 (c)(1),
(2) Date: Oct. 22, 2015

(87) PCT Pub. No.: WO2014/176276
PCT Pub. Date: Oct. 30, 2014

(65) Prior Publication Data
US 2016/0074496 A1 Mar. 17, 2016

Related U.S. Application Data

(60) Provisional application No. 61/814,740, filed on Apr. 22, 2013.

(51) Int. Cl.
| | |
|---|---|
| *A61K 39/00* | (2006.01) |
| *A61K 39/38* | (2006.01) |
| *A61K 39/02* | (2006.01) |
| *A61K 39/08* | (2006.01) |
| *A01N 63/00* | (2006.01) |
| *C07K 16/12* | (2006.01) |
| *A61K 38/48* | (2006.01) |

(52) U.S. Cl.
CPC .......... *A61K 39/08* (2013.01); *C07K 16/1282* (2013.01); *A61K 38/4893* (2013.01); *A61K 2039/545* (2013.01); *A61K 2039/55566* (2013.01); *A61K 2039/58* (2013.01); *C07K 2317/76* (2013.01)

(58) Field of Classification Search
CPC .... A61K 38/00; A61K 38/4893; A61K 39/08; A61K 35/74; C07K 14/33
See application file for complete search history.

(56) References Cited

U.S. PATENT DOCUMENTS

| | | | |
|---|---|---|---|
| 2004/0028705 A1* | 2/2004 | Ballard | C07K 14/33 424/239.1 |
| 2012/0070859 A1* | 3/2012 | Ballard | C12N 15/70 435/69.1 |
| 2012/0269841 A1* | 10/2012 | Sidhu | C07K 14/33 424/190.1 |
| 2013/0004561 A1* | 1/2013 | Shone | C07K 16/1282 424/450 |
| 2013/0230537 A1* | 9/2013 | Hussack | C07K 16/1282 424/167.1 |
| 2013/0266583 A1* | 10/2013 | Shone | C07K 14/33 424/167.1 |
| 2015/0044250 A1* | 2/2015 | Heinrichs | C07K 14/33 424/190.1 |

FOREIGN PATENT DOCUMENTS

| | | |
|---|---|---|
| WO | WO-2010094970 A1 | 8/2010 |
| WO | WO-2011/130650 A2 | 10/2011 |
| WO | WO 2013/038156 * | 3/2013 |
| WO | WO-2013/038156 A1 | 3/2013 |

OTHER PUBLICATIONS

Vedantam et al., Gut microbes, 2012; 3(2): 121-134.*
Vohra et al., Induction of cytokines in a macrophage cell line by proteins of Clostridium difficile, FEMS Immunol. Med. Microbiol., 65: 96-104 (2012).

* cited by examiner

*Primary Examiner* — Gary B Nickol
*Assistant Examiner* — Lakia J Jackson-Tongue
(74) *Attorney, Agent, or Firm* — Winstead PC

(57) ABSTRACT

Embodiments of the present disclosure include vaccine compositions comprising a TcdB toxin or toxoid derived therefrom. The TcdB toxin may be derived from a hypervirulent strain of *C. difficile*. A further embodiment is directed to a method of conferring an active immunity against a *C. difficile* infection in a subject by administering the vaccine composition to the subject.

4 Claims, 7 Drawing Sheets
Specification includes a Sequence Listing.

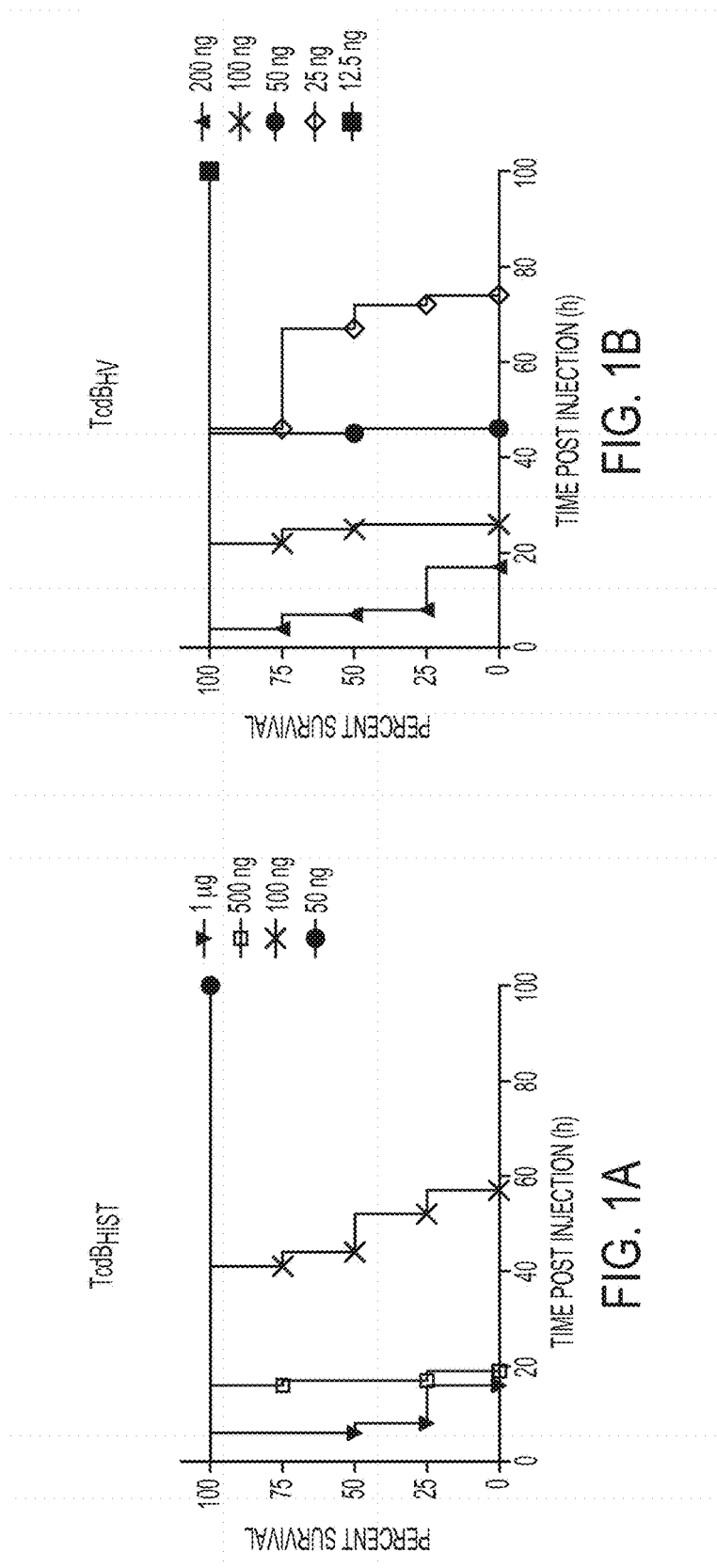

SURVIVAL TIME

| | >100 h | <10 h | 16-28 h | 40-60 h |

TcdB$_{HIST}$

TcdB$_{HV}$

FIG. 2A

CEREBRUM   CEREBELLUM

TcdB$_{HIST}$

TcdB$_{HV}$

FIG. 2B

```
MSLVNRKQLEKMANVRFRVQEDEYVAILDALEEYHNMSENTVVEKYLKLKDINSLTDIYI
DTYKKSGRNKALKKFKEYLVTEVLELKNNNLTPVEKNLHFVWIGGQINDTAINYINQWKD
VNSDYNVNVFYDSNAFLINTLKKTIVESATNDTLESFRENLNDPRFDYNKFYRKRMEIIY
DKQKNFINYYKTQREENPDLIIDDIVKIYLSNEYSKDIDELNSYIEESLNKVTENSGNDV
RNFEEFKGGESFKLYEQELVERWNLAAASDILRISALKEVGGVYLDVDMLPGIQPDLFES
IEKPSSVTVDFWEMVKLEAIMKYKEYIPGYTSEHFDMLDEEVQSSFESVLASKSDKSEIF
SSLGDMEASPLEVKIAFNSKGIINQGLISVKDSYCSNLIVKQIENRYKILNNSLNPAISE
DNDFNTTTNAFIDSIMAEANADNGRFMMELGKYLRVGFFPDVKTTINLSGPEAYAAAYQD
LLMFKEGSMNIHLIEADLRNFEISKTNISQSTEQEMASLWSFDDARAKAQFEEYKKNYFE
GSLGEDDNLDFSQNTVVDKEYLLEKISSLARSSERGYIHYIVQLQGDKISYEAACNLFAK
TPYDSVLFQKNIEDSEIAYYYNPGDGEIQEIDKYKIPSIISDRPKIKLTFIGHGKDEFNT
DIFAGLDVDSLSTEIETAIDLAKEDISPKSIEINLLGCNMFSYSVNVEETYPGKLLLRVK
DKVSELMPSISQDSIIVSANQYEVRINSEGRRELLDHSGEWINKEESIIKDISSKEYISF
NPKENKIIVKSKNLPELSTLLQEIRNNSNSSDIELEEKVMLAECEINVISNIDTQVVEGR
IEEAKSLTSDSINYIKNEFKLIESISDALYDLKQQNELEESHFISFEDILETDEGFSIRF
IDKETGESIFVETEKAIFSEYANHITEEISKIKGTIFDTVNGKLVKKVNLDATHEVNTLN
AAFFIQSLIEYNSSKESLSNLSVAMKVQVYAQLFSTGLNTITDAAKVVELVSTALDETID
LLPTLSEGLPVIATIIDGVSLGAAIKELSETSDPLLRQEIEAKIGIMAVNLTAATTAIIT
SSLGIASGFSILLVPLAGISAGIPSLVNNELILRDKATKVVDYFSHISLAESEGAFTSLD
DKIMMPQDDLVISEIDFNNNSITLGKCEIWRMEGGSGHTVTDDIDHFFSAPSITYREPHL
SIYDVLEVQKEELDLSKDLMVLPNAPNRVFAWETGWTPGLRSLENDGTKLLDRIRDNYEG
EFYWRYFAFIADALITTLKPRYEDTNIRINLDSNTRSFIVPVITTEYIREKLSYSFYGSG
GTYALSLSQYNMNINIELNENDTWVIDVDNVVRDVTIESDKIKKGDLIENILSKLSIEDN
KIILDNHEINFSGTLNGGNGFVSLTFSILEGINAVIEVDLLSKSYKVLISGELKTLMANS
NSVQQKIDYIGLNSELQKNIPYSFMDDKGKENGFINCSTKEGLFVSELSDVVLISKVYMD
NSKPLFGYCSNDLKDVKVITKDDVIILTGYYLKDDIKISLSFTIQDENTIKLNGVYLDEN
GVAEILKFMNKKGSTNTSDSLMSFLESMNIKSIFINSLQSNTKLILDTNFIISGTTSIGQ
FEFICDKDNNIQPYFIKFNTLETKYTLYVGNRQNMIVEPNYDLDDSGDISSTVINFSQKY
LYGIDSCVNKVIISPNIYTDEINITPIYEANNTYPEVIVLDTNYISEKININDLSIRY
VWSNDGSDFILMSTDEENKVSQVKIRFTNVFKGNTISDKISFNFSDKQDVSINKVISTFT
PSYYVEGLLNYDLGLISLYNEKFYINNFGMMVSGLVYINDSLYYFKPPIKNLITGFTTIG
DDKYYFNPDNGGAASVGETIIDGKNYYFSQNGVLQTGVFSTEDGFKYFAPADTLDENLEG
EAIDFTGKLTIDENVYYFGDNYRAAIEWQTLDDEVYYFSTDTGRAFKGLNQIGDDKFYFN
SDGIMQKGFVNINDKTFYFDDSGVMKSGYTEIDGKYFYFAENGEMQIGVFNTADGFKYFA
HHDEDLGNEEGEALSYSGILNFNNKIYYFDDSFTAVVGWKDLEDGSKYYFDEDTAEAYIG
ISIINDGKYYFNDSGIMQIGFVTINNEVFYPSDSGIVESGMQNIDDNYFYIDENGLVQIG
VFDTSDGYKYFAPANTVNDNIYGQAVEYSGLVRVGEDVYYFGETYTIETGWIYDMENESD
KYYFDPETKKAYKGINVIDDIKYYFDENGIMRTGLITFEDNHYYFNEDGIMQYGYLNIED
KTFYFSEDGIMQIGVFNTPDGFKYFAHQNTLDENFEGESINYTGWLDLDEKRYYFTDEYI
AATGSVIIDGEEYYFDPDTAQLVISE
```

FIG. 7

SEQUENCE LISTING

```
<160> NUMBER OF SEQ ID NOS: 30

<210> SEQ ID NO 1
<211> LENGTH: 2366
<212> TYPE: PRT
<213> ORGANISM: Clostridium difficile
<220> FEATURE:
<221> NAME/KEY: PEPTIDE
<222> LOCATION: (1)..(2366)

<400> SEQUENCE: 1

Met Ser Leu Val Asn Arg Lys Gln Leu Glu Lys Met Ala Asn Val Arg
1               5                   10                  15

Phe Arg Val Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
```

-continued

```
            130                 135                 140
Ile Val Glu Ser Ala Thr Asn Asp Thr Leu Glu Ser Phe Arg Glu Asn
145                 150                 155                 160

Leu Asn Asp Pro Arg Phe Asp Tyr Asn Lys Phe Tyr Arg Lys Arg Met
                165                 170                 175

Glu Ile Ile Tyr Asp Lys Gln Lys Asn Phe Ile Asn Tyr Tyr Lys Thr
                180                 185                 190

Gln Arg Glu Glu Asn Pro Asp Leu Ile Ile Asp Asp Ile Val Lys Ile
            195                 200                 205

Tyr Leu Ser Asn Glu Tyr Ser Lys Asp Ile Asp Glu Leu Asn Ser Tyr
        210                 215                 220

Ile Glu Glu Ser Leu Asn Lys Val Thr Glu Asn Ser Gly Asn Asp Val
225                 230                 235                 240

Arg Asn Phe Glu Glu Phe Lys Gly Gly Glu Ser Phe Lys Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Val Gly Gly Val Tyr Leu Asp Val Asp
        275                 280                 285

Met Leu Pro Gly Ile Gln Pro Asp Leu Phe Glu Ser Ile Glu Lys Pro
        290                 295                 300

Ser Ser Val Thr Val Asp Phe Trp Glu Met Val Lys Leu Glu Ala Ile
305                 310                 315                 320

Met Lys Tyr Lys Glu Tyr Ile Pro Gly Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
        370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Ala Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
        450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Lys Asn Tyr Phe Glu Gly Ser Leu Gly
        530                 535                 540

Glu Asp Asp Asn Leu Asp Phe Ser Gln Asn Thr Val Val Asp Lys Glu
545                 550                 555                 560
```

```
Tyr Leu Leu Glu Lys Ile Ser Ser Leu Ala Arg Ser Glu Arg Gly
            565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
            595                 600                 605

Gln Lys Asn Ile Glu Asp Ser Glu Ile Ala Tyr Tyr Tyr Asn Pro Gly
            610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
            645                 650                 655

Glu Phe Asn Thr Asp Ile Phe Ala Gly Leu Asp Val Asp Ser Leu Ser
            660                 665                 670

Thr Glu Ile Glu Thr Ala Ile Asp Leu Ala Lys Glu Asp Ile Ser Pro
            675                 680                 685

Lys Ser Ile Glu Ile Asn Leu Leu Gly Cys Asn Met Phe Ser Tyr Ser
            690                 695                 700

Val Asn Val Glu Glu Thr Tyr Pro Gly Lys Leu Leu Leu Arg Val Lys
705                 710                 715                 720

Asp Lys Val Ser Glu Leu Met Pro Ser Ile Ser Gln Asp Ser Ile Ile
            725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
            755                 760                 765

Ile Lys Asp Ile Ser Ser Lys Glu Tyr Ile Ser Phe Asn Pro Lys Glu
            770                 775                 780

Asn Lys Ile Ile Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
            805                 810                 815

Glu Lys Val Met Leu Ala Glu Cys Glu Ile Asn Val Ile Ser Asn Ile
            820                 825                 830

Asp Thr Gln Val Val Glu Gly Arg Ile Glu Glu Ala Lys Ser Leu Thr
            835                 840                 845

Ser Asp Ser Ile Asn Tyr Ile Lys Asn Glu Phe Lys Leu Ile Glu Ser
850                 855                 860

Ile Ser Asp Ala Leu Tyr Asp Leu Lys Gln Gln Asn Glu Leu Glu Glu
865                 870                 875                 880

Ser His Phe Ile Ser Phe Glu Asp Ile Leu Glu Thr Asp Glu Gly Phe
            885                 890                 895

Ser Ile Arg Phe Ile Asp Lys Glu Thr Gly Glu Ser Ile Phe Val Glu
            900                 905                 910

Thr Glu Lys Ala Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
            930                 935                 940

Val Lys Lys Val Asn Leu Asp Ala Thr His Glu Val Asn Thr Leu Asn
945                 950                 955                 960

Ala Ala Phe Phe Ile Gln Ser Leu Ile Glu Tyr Asn Ser Ser Lys Glu
            965                 970                 975
```

```
Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
            995                1000                1005

Glu Leu Val Ser Thr Ala Leu Asp Glu Thr Ile Asp Leu Leu Pro
           1010                1015                1020

Thr Leu Ser Glu Gly Leu Pro Val Ile Ala Thr Ile Ile Asp Gly
           1025                1030                1035

Val Ser Leu Gly Ala Ala Ile Lys Glu Leu Ser Glu Thr Ser Asp
           1040                1045                1050

Pro Leu Leu Arg Gln Glu Ile Glu Ala Lys Ile Gly Ile Met Ala
           1055                1060                1065

Val Asn Leu Thr Ala Ala Thr Thr Ala Ile Ile Thr Ser Ser Leu
           1070                1075                1080

Gly Ile Ala Ser Gly Phe Ser Ile Leu Leu Val Pro Leu Ala Gly
           1085                1090                1095

Ile Ser Ala Gly Ile Pro Ser Leu Val Asn Asn Glu Leu Ile Leu
           1100                1105                1110

Arg Asp Lys Ala Thr Lys Val Val Asp Tyr Phe Ser His Ile Ser
           1115                1120                1125

Leu Ala Glu Ser Glu Gly Ala Phe Thr Ser Leu Asp Asp Lys Ile
           1130                1135                1140

Met Met Pro Gln Asp Asp Leu Val Ile Ser Glu Ile Asp Phe Asn
           1145                1150                1155

Asn Asn Ser Ile Thr Leu Gly Lys Cys Glu Ile Trp Arg Met Glu
           1160                1165                1170

Gly Gly Ser Gly His Thr Val Thr Asp Asp Ile Asp His Phe Phe
           1175                1180                1185

Ser Ala Pro Ser Ile Thr Tyr Arg Glu Pro His Leu Ser Ile Tyr
           1190                1195                1200

Asp Val Leu Glu Val Gln Lys Glu Glu Leu Asp Leu Ser Lys Asp
           1205                1210                1215

Leu Met Val Leu Pro Asn Ala Pro Asn Arg Val Phe Ala Trp Glu
           1220                1225                1230

Thr Gly Trp Thr Pro Gly Leu Arg Ser Leu Glu Asn Asp Gly Thr
           1235                1240                1245

Lys Leu Leu Asp Arg Ile Arg Asp Asn Tyr Glu Gly Glu Phe Tyr
           1250                1255                1260

Trp Arg Tyr Phe Ala Phe Ile Ala Asp Ala Leu Ile Thr Thr Leu
           1265                1270                1275

Lys Pro Arg Tyr Glu Asp Thr Asn Ile Arg Ile Asn Leu Asp Ser
           1280                1285                1290

Asn Thr Arg Ser Phe Ile Val Pro Val Ile Thr Thr Glu Tyr Ile
           1295                1300                1305

Arg Glu Lys Leu Ser Tyr Ser Phe Tyr Gly Ser Gly Gly Thr Tyr
           1310                1315                1320

Ala Leu Ser Leu Ser Gln Tyr Asn Met Asn Ile Asn Ile Glu Leu
           1325                1330                1335

Asn Glu Asn Asp Thr Trp Val Ile Asp Val Asp Asn Val Val Arg
           1340                1345                1350

Asp Val Thr Ile Glu Ser Asp Lys Ile Lys Lys Gly Asp Leu Ile
           1355                1360                1365

Glu Asn Ile Leu Ser Lys Leu Ser Ile Glu Asp Asn Lys Ile Ile
```

-continued

```
            1370                1375                1380
Leu Asp Asn His Glu Ile Asn Phe Ser Gly Thr Leu Asn Gly Gly
    1385                1390                1395
Asn Gly Phe Val Ser Leu Thr Phe Ser Ile Leu Glu Gly Ile Asn
    1400                1405                1410
Ala Val Ile Glu Val Asp Leu Leu Ser Lys Ser Tyr Lys Val Leu
    1415                1420                1425
Ile Ser Gly Glu Leu Lys Thr Leu Met Ala Asn Ser Asn Ser Val
    1430                1435                1440
Gln Gln Lys Ile Asp Tyr Ile Gly Leu Asn Ser Glu Leu Gln Lys
    1445                1450                1455
Asn Ile Pro Tyr Ser Phe Met Asp Asp Lys Gly Lys Glu Asn Gly
    1460                1465                1470
Phe Ile Asn Cys Ser Thr Lys Glu Gly Leu Phe Val Ser Glu Leu
    1475                1480                1485
Ser Asp Val Val Leu Ile Ser Lys Val Tyr Met Asp Asn Ser Lys
    1490                1495                1500
Pro Leu Phe Gly Tyr Cys Ser Asn Asp Leu Lys Asp Val Lys Val
    1505                1510                1515
Ile Thr Lys Asp Asp Val Ile Ile Leu Thr Gly Tyr Tyr Leu Lys
    1520                1525                1530
Asp Asp Ile Lys Ile Ser Leu Ser Phe Thr Ile Gln Asp Glu Asn
    1535                1540                1545
Thr Ile Lys Leu Asn Gly Val Tyr Leu Asp Glu Asn Gly Val Ala
    1550                1555                1560
Glu Ile Leu Lys Phe Met Asn Lys Lys Gly Ser Thr Asn Thr Ser
    1565                1570                1575
Asp Ser Leu Met Ser Phe Leu Glu Ser Met Asn Ile Lys Ser Ile
    1580                1585                1590
Phe Ile Asn Ser Leu Gln Ser Asn Thr Lys Leu Ile Leu Asp Thr
    1595                1600                1605
Asn Phe Ile Ile Ser Gly Thr Thr Ser Ile Gly Gln Phe Glu Phe
    1610                1615                1620
Ile Cys Asp Lys Asp Asn Asn Ile Gln Pro Tyr Phe Ile Lys Phe
    1625                1630                1635
Asn Thr Leu Glu Thr Lys Tyr Thr Leu Tyr Val Gly Asn Arg Gln
    1640                1645                1650
Asn Met Ile Val Glu Pro Asn Tyr Asp Leu Asp Asp Ser Gly Asp
    1655                1660                1665
Ile Ser Ser Thr Val Ile Asn Phe Ser Gln Lys Tyr Leu Tyr Gly
    1670                1675                1680
Ile Asp Ser Cys Val Asn Lys Val Ile Ile Ser Pro Asn Ile Tyr
    1685                1690                1695
Thr Asp Glu Ile Asn Ile Thr Pro Ile Tyr Glu Ala Asn Asn Thr
    1700                1705                1710
Tyr Pro Glu Val Ile Val Leu Asp Thr Asn Tyr Ile Ser Glu Lys
    1715                1720                1725
Ile Asn Ile Asn Ile Asn Asp Leu Ser Ile Arg Tyr Val Trp Ser
    1730                1735                1740
Asn Asp Gly Ser Asp Phe Ile Leu Met Ser Thr Asp Glu Glu Asn
    1745                1750                1755
Lys Val Ser Gln Val Lys Ile Arg Phe Thr Asn Val Phe Lys Gly
    1760                1765                1770
```

```
-continued

Asn Thr Ile Ser Asp Lys Ile Ser Phe Asn Phe Ser Asp Lys Gln
    1775            1780            1785

Asp Val Ser Ile Asn Lys Val Ile Ser Thr Phe Thr Pro Ser Tyr
    1790            1795            1800

Tyr Val Glu Gly Leu Leu Asn Tyr Asp Leu Gly Leu Ile Ser Leu
    1805            1810            1815

Tyr Asn Glu Lys Phe Tyr Ile Asn Asn Phe Gly Met Met Val Ser
    1820            1825            1830

Gly Leu Val Tyr Ile Asn Asp Ser Leu Tyr Tyr Phe Lys Pro Pro
    1835            1840            1845

Ile Lys Asn Leu Ile Thr Gly Phe Thr Thr Ile Gly Asp Asp Lys
    1850            1855            1860

Tyr Tyr Phe Asn Pro Asp Asn Gly Gly Ala Ala Ser Val Gly Glu
    1865            1870            1875

Thr Ile Ile Asp Gly Lys Asn Tyr Tyr Phe Ser Gln Asn Gly Val
    1880            1885            1890

Leu Gln Thr Gly Val Phe Ser Thr Glu Asp Gly Phe Lys Tyr Phe
    1895            1900            1905

Ala Pro Ala Asp Thr Leu Asp Glu Asn Leu Glu Gly Glu Ala Ile
    1910            1915            1920

Asp Phe Thr Gly Lys Leu Thr Ile Asp Glu Asn Val Tyr Tyr Phe
    1925            1930            1935

Gly Asp Asn Tyr Arg Ala Ala Ile Glu Trp Gln Thr Leu Asp Asp
    1940            1945            1950

Glu Val Tyr Tyr Phe Ser Thr Asp Thr Gly Arg Ala Phe Lys Gly
    1955            1960            1965

Leu Asn Gln Ile Gly Asp Asp Lys Phe Tyr Phe Asn Ser Asp Gly
    1970            1975            1980

Ile Met Gln Lys Gly Phe Val Asn Ile Asn Asp Lys Thr Phe Tyr
    1985            1990            1995

Phe Asp Asp Ser Gly Val Met Lys Ser Gly Tyr Thr Glu Ile Asp
    2000            2005            2010

Gly Lys Tyr Phe Tyr Phe Ala Glu Asn Gly Glu Met Gln Ile Gly
    2015            2020            2025

Val Phe Asn Thr Ala Asp Gly Phe Lys Tyr Phe Ala His His Asp
    2030            2035            2040

Glu Asp Leu Gly Asn Glu Glu Gly Glu Ala Leu Ser Tyr Ser Gly
    2045            2050            2055

Ile Leu Asn Phe Asn Asn Lys Ile Tyr Tyr Phe Asp Asp Ser Phe
    2060            2065            2070

Thr Ala Val Val Gly Trp Lys Asp Leu Glu Asp Gly Ser Lys Tyr
    2075            2080            2085

Tyr Phe Asp Glu Asp Thr Ala Glu Ala Tyr Ile Gly Ile Ser Ile
    2090            2095            2100

Ile Asn Asp Gly Lys Tyr Tyr Phe Asn Asp Ser Gly Ile Met Gln
    2105            2110            2115

Ile Gly Phe Val Thr Ile Asn Asn Glu Val Phe Tyr Phe Ser Asp
    2120            2125            2130

Ser Gly Ile Val Glu Ser Gly Met Gln Asn Ile Asp Asp Asn Tyr
    2135            2140            2145

Phe Tyr Ile Asp Glu Asn Gly Leu Val Gln Ile Gly Val Phe Asp
    2150            2155            2160
```

-continued

```
Thr Ser Asp Gly Tyr Lys Tyr Phe Ala Pro Ala Asn Thr Val Asn
    2165                2170                2175

Asp Asn Ile Tyr Gly Gln Ala Val Glu Tyr Ser Gly Leu Val Arg
    2180                2185                2190

Val Gly Glu Asp Val Tyr Tyr Phe Gly Glu Thr Tyr Thr Ile Glu
    2195                2200                2205

Thr Gly Trp Ile Tyr Asp Met Glu Asn Glu Ser Asp Lys Tyr Tyr
    2210                2215                2220

Phe Asp Pro Glu Thr Lys Lys Ala Tyr Lys Gly Ile Asn Val Ile
    2225                2230                2235

Asp Asp Ile Lys Tyr Tyr Phe Asp Glu Asn Gly Ile Met Arg Thr
    2240                2245                2250

Gly Leu Ile Thr Phe Glu Asp Asn His Tyr Tyr Phe Asn Glu Asp
    2255                2260                2265

Gly Ile Met Gln Tyr Gly Tyr Leu Asn Ile Glu Asp Lys Thr Phe
    2270                2275                2280

Tyr Phe Ser Glu Asp Gly Ile Met Gln Ile Gly Val Phe Asn Thr
    2285                2290                2295

Pro Asp Gly Phe Lys Tyr Phe Ala His Gln Asn Thr Leu Asp Glu
    2300                2305                2310

Asn Phe Glu Gly Glu Ser Ile Asn Tyr Thr Gly Trp Leu Asp Leu
    2315                2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Tyr Phe Asp Pro Asp
    2345                2350                2355

Thr Ala Gln Leu Val Ile Ser Glu
    2360                2365

<210> SEQ ID NO 2
<211> LENGTH: 18
<212> TYPE: PRT
<213> ORGANISM: Clostridium difficile
<220> FEATURE:
<221> NAME/KEY: PEPTIDE
<222> LOCATION: (1)..(18)

<400> SEQUENCE: 2

Ser Pro Asn Ile Tyr Thr Asp Glu Ile Asn Ile Thr Pro Ile Tyr Glu
1               5                   10                  15

Ala Asn

<210> SEQ ID NO 3
<211> LENGTH: 18
<212> TYPE: PRT
<213> ORGANISM: Clostridium difficile
<220> FEATURE:
<221> NAME/KEY: PEPTIDE
<222> LOCATION: (1)..(18)

<400> SEQUENCE: 3

Ser Pro Asn Ile Tyr Thr Asp Glu Ile Asn Ile Thr Pro Val Tyr Glu
1               5                   10                  15

Thr Asn

<210> SEQ ID NO 4
<211> LENGTH: 16
<212> TYPE: PRT
<213> ORGANISM: Clostridium difficile
```

```
<220> FEATURE:
<221> NAME/KEY: PEPTIDE
<222> LOCATION: (1)..(16)

<400> SEQUENCE: 4

Tyr Pro Glu Val Ile Val Leu Asp Thr Asn Tyr Ile Ser Glu Lys Ile
1               5                   10                  15

<210> SEQ ID NO 5
<211> LENGTH: 16
<212> TYPE: PRT
<213> ORGANISM: Clostridium difficile
<220> FEATURE:
<221> NAME/KEY: PEPTIDE
<222> LOCATION: (1)..(16)

<400> SEQUENCE: 5

Tyr Pro Glu Val Ile Val Leu Asp Ala Asn Tyr Ile Asn Glu Lys Ile
1               5                   10                  15

<210> SEQ ID NO 6
<211> LENGTH: 20
<212> TYPE: PRT
<213> ORGANISM: Clostridium difficile
<220> FEATURE:
<221> NAME/KEY: PEPTIDE
<222> LOCATION: (1)..(20)

<400> SEQUENCE: 6

Ala Ser Val Gly Glu Thr Ile Ile Asp Gly Lys Asn Tyr Tyr Phe Ser
1               5                   10                  15

Gln Asn Gly Val
            20

<210> SEQ ID NO 7
<211> LENGTH: 20
<212> TYPE: PRT
<213> ORGANISM: Clostridium difficile
<220> FEATURE:
<221> NAME/KEY: PEPTIDE
<222> LOCATION: (1)..(20)

<400> SEQUENCE: 7

Ala Ser Ile Gly Glu Thr Ile Ile Asp Asp Lys Asn Tyr Tyr Phe Asn
1               5                   10                  15

Gln Ser Gly Val
            20

<210> SEQ ID NO 8
<211> LENGTH: 15
<212> TYPE: PRT
<213> ORGANISM: Clostridium difficile
<220> FEATURE:
<221> NAME/KEY: PEPTIDE
<222> LOCATION: (1)..(15)

<400> SEQUENCE: 8

Thr Ile Gly Asp Asp Lys Tyr Tyr Phe Asn Pro Asp Asn Gly Gly
1               5                   10                  15

<210> SEQ ID NO 9
<211> LENGTH: 15
<212> TYPE: PRT
<213> ORGANISM: Clostridium difficile
<220> FEATURE:
<221> NAME/KEY: PEPTIDE
<222> LOCATION: (1)..(15)
```

```
<400> SEQUENCE: 9

Thr Val Gly Asp Asp Lys Tyr Tyr Phe Asn Pro Ile Asn Gly Gly
1               5                   10                  15

<210> SEQ ID NO 10
<211> LENGTH: 12
<212> TYPE: PRT
<213> ORGANISM: Clostridium difficile
<220> FEATURE:
<221> NAME/KEY: PEPTIDE
<222> LOCATION: (1)..(12)

<400> SEQUENCE: 10

Pro Ala Asp Thr Leu Asp Glu Asn Leu Glu Gly Glu
1               5                   10

<210> SEQ ID NO 11
<211> LENGTH: 12
<212> TYPE: PRT
<213> ORGANISM: Clostridium difficile
<220> FEATURE:
<221> NAME/KEY: PEPTIDE
<222> LOCATION: (1)..(12)

<400> SEQUENCE: 11

Pro Ala Asp Thr Leu Asp Glu Asn Leu Glu Gly Glu
1               5                   10

<210> SEQ ID NO 12
<211> LENGTH: 12
<212> TYPE: PRT
<213> ORGANISM: Clostridium difficile
<220> FEATURE:
<221> NAME/KEY: PEPTIDE
<222> LOCATION: (1)..(12)

<400> SEQUENCE: 12

Ala Ile Asp Phe Thr Gly Lys Leu Thr Ile Asp Glu
1               5                   10

<210> SEQ ID NO 13
<211> LENGTH: 12
<212> TYPE: PRT
<213> ORGANISM: Clostridium difficile
<220> FEATURE:
<221> NAME/KEY: PEPTIDE
<222> LOCATION: (1)..(12)

<400> SEQUENCE: 13

Ala Ile Asp Phe Thr Gly Lys Leu Ile Ile Asp Glu
1               5                   10

<210> SEQ ID NO 14
<211> LENGTH: 14
<212> TYPE: PRT
<213> ORGANISM: Clostridium difficile
<220> FEATURE:
<221> NAME/KEY: PEPTIDE
<222> LOCATION: (1)..(14)

<400> SEQUENCE: 14

Asn Val Tyr Tyr Phe Gly Asp Asn Tyr Arg Ala Ala Ile Glu
1               5                   10

<210> SEQ ID NO 15
<211> LENGTH: 14
```

```
<212> TYPE: PRT
<213> ORGANISM: Clostridium difficile
<220> FEATURE:
<221> NAME/KEY: PEPTIDE
<222> LOCATION: (1)..(14)

<400> SEQUENCE: 15

Asn Ile Tyr Tyr Phe Asp Asp Asn Tyr Arg Gly Ala Val Glu
1               5                   10

<210> SEQ ID NO 16
<211> LENGTH: 12
<212> TYPE: PRT
<213> ORGANISM: Clostridium difficile
<220> FEATURE:
<221> NAME/KEY: PEPTIDE
<222> LOCATION: (1)..(12)

<400> SEQUENCE: 16

Tyr Tyr Phe Ser Thr Asp Thr Gly Arg Ala Phe Lys
1               5                   10

<210> SEQ ID NO 17
<211> LENGTH: 12
<212> TYPE: PRT
<213> ORGANISM: Clostridium difficile
<220> FEATURE:
<221> NAME/KEY: PEPTIDE
<222> LOCATION: (1)..(12)

<400> SEQUENCE: 17

His Tyr Phe Ser Pro Glu Thr Gly Lys Ala Phe Lys
1               5                   10

<210> SEQ ID NO 18
<211> LENGTH: 14
<212> TYPE: PRT
<213> ORGANISM: Clostridium difficile
<220> FEATURE:
<221> NAME/KEY: PEPTIDE
<222> LOCATION: (1)..(14)

<400> SEQUENCE: 18

Ile Gly Asp Asp Lys Phe Tyr Phe Asn Ser Asp Gly Ile Met
1               5                   10

<210> SEQ ID NO 19
<211> LENGTH: 14
<212> TYPE: PRT
<213> ORGANISM: Clostridium difficile
<220> FEATURE:
<221> NAME/KEY: PEPTIDE
<222> LOCATION: (1)..(14)

<400> SEQUENCE: 19

Ile Gly Asp Tyr Lys Tyr Tyr Phe Asn Ser Asp Gly Val Met
1               5                   10

<210> SEQ ID NO 20
<211> LENGTH: 22
<212> TYPE: PRT
<213> ORGANISM: Clostridium difficile
<220> FEATURE:
<221> NAME/KEY: PEPTIDE
<222> LOCATION: (1)..(22)

<400> SEQUENCE: 20

Tyr Phe Tyr Phe Ala Glu Asn Gly Glu Met Gln Ile Gly Val Phe Asn
```

```
1               5                   10                  15
Thr Ala Asp Gly Phe Lys
            20

<210> SEQ ID NO 21
<211> LENGTH: 22
<212> TYPE: PRT
<213> ORGANISM: Clostridium difficile
<220> FEATURE:
<221> NAME/KEY: PEPTIDE
<222> LOCATION: (1)..(22)

<400> SEQUENCE: 21

His Phe Tyr Phe Ala Glu Asn Gly Glu Met Gln Ile Gly Val Phe Asn
1               5                   10                  15

Thr Glu Asp Gly Phe Lys
            20

<210> SEQ ID NO 22
<211> LENGTH: 16
<212> TYPE: PRT
<213> ORGANISM: Clostridium difficile
<220> FEATURE:
<221> NAME/KEY: PEPTIDE
<222> LOCATION: (1)..(16)

<400> SEQUENCE: 22

Ile Asn Asp Gly Lys Tyr Tyr Phe Asn Asp Ser Gly Ile Met Gln Ile
1               5                   10                  15

<210> SEQ ID NO 23
<211> LENGTH: 16
<212> TYPE: PRT
<213> ORGANISM: Clostridium difficile
<220> FEATURE:
<221> NAME/KEY: PEPTIDE
<222> LOCATION: (1)..(16)

<400> SEQUENCE: 23

Ile Asn Asp Gly Gln Tyr Tyr Phe Asn Asp Asp Gly Ile Met Gln Val
1               5                   10                  15

<210> SEQ ID NO 24
<211> LENGTH: 16
<212> TYPE: PRT
<213> ORGANISM: Clostridium difficile
<220> FEATURE:
<221> NAME/KEY: PEPTIDE
<222> LOCATION: (1)..(16)

<400> SEQUENCE: 24

Glu Asn Glu Ser Asp Lys Tyr Tyr Phe Asp Pro Glu Thr Lys Lys Ala
1               5                   10                  15

<210> SEQ ID NO 25
<211> LENGTH: 16
<212> TYPE: PRT
<213> ORGANISM: Clostridium difficile
<220> FEATURE:
<221> NAME/KEY: PEPTIDE
<222> LOCATION: (1)..(16)

<400> SEQUENCE: 25

Glu Asn Glu Ser Asp Lys Tyr Tyr Phe Asn Pro Glu Thr Lys Lys Ala
1               5                   10                  15
```

```
<210> SEQ ID NO 26
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 26

Asp Asn His Tyr Tyr Phe Asn Glu Asp Gly Ile Met Gln Tyr Gly Tyr
1               5                   10                  15

Leu Asn Ile

<210> SEQ ID NO 27
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 27

Asn Asn Asn Tyr Tyr Phe Asn Glu Asn Gly Glu Met Gln Phe Gly Tyr
1               5                   10                  15

Ile Asn Ile

<210> SEQ ID NO 28
<211> LENGTH: 18
<212> TYPE: PRT
<213> ORGANISM: Clostridium difficile
<220> FEATURE:
<221> NAME/KEY: PEPTIDE
<222> LOCATION: (1)..(18)

<400> SEQUENCE: 28

Ala His Gln Asn Thr Leu Asp Glu Asn Phe Glu Gly Glu Ser Ile Asn
1               5                   10                  15

Tyr Thr

<210> SEQ ID NO 29
<211> LENGTH: 26
<212> TYPE: DNA
<213> ORGANISM: Artificial Sequence
<220> FEATURE:
<223> OTHER INFORMATION: Primer

<400> SEQUENCE: 29
gatcatatgc tgtatgtggg taaccg                                    26

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
aacggatcct tattcgctaa taacca                                    26
```

CLOSTRIDIUM DIFFICILE VACCINE AND METHODS OF USE

CROSS-REFERENCES TO RELATED APPLICATIONS

This application claims the benefit under 35 U.S.C. § 119(e) of U.S. Provisional Patent Application No. 61/814,740 filed Apr. 22, 2013 which is incorporated herein by reference in its entirety as if fully set forth herein.

BACKGROUND

*Clostridium difficile* is the leading cause of hospital-acquired diarrhea in developed countries. This spore-forming anaerobic bacterium contaminates hospital environments and infects patients undergoing antibiotic therapy within health care facilities. Despite these problems, historically, treatment with antibiotics such as metronidazole and vancomycin has been an effective means of treating this disease. Yet, disturbing trends of increased morbidity and mortality, as well relapse of *C. difficile* infected patients have become apparent over the past decade. These trends correlate with an increase in the number of patients infected by a hypervirulent strain of *C. difficile*. This *C. difficile* strain, often referred to as the BI/NAP1/027 strain, has now been found in a majority of states in the US and is prominent both in Europe and Canada. To date, many factors such as antibiotic resistance, sporulation ability, and toxin production have been proposed to contribute to the difference in virulence of historical and hypervirulent *C. difficile*. Yet, the relevance of these factors is still greatly debated, leaving us with a poor understanding into how this emergent strain correlates with increased mortality.

*C. difficile* produces two large clostridial toxins, TcdA and TcdB, which cause extensive tissue damage and ultimately lead to human disease. Our work has focused on understanding how variations in the toxins produced by historical and epidemic strains change the extent of *C. difficile* virulence. Of particular interest are the differences in the sequence and activities of TcdB, which has been implicated as a critical *C. difficile* virulence factor.

TcdB is a single chain polypeptide toxin where the glucosyltransferase domain is located at the N-terminus (GTD: 1-543), followed by an autoprocessing site between amino acid 543 and 544 which is subject to intramolecular cleavage by the cysteine protease domain (CPD: 544-807), a hydrophobic transmembrane domain (TMD: 956-1128), and a putative receptor binding domain at the C-terminus (CTD: 1651-2366). The gene encoding TcdB is located within a pathogenecity locus on the chromosome of *C. difficile* along with genes encoding TcdA (enterotoxin), TcdE, and regulators of toxin gene expression (TcdC and TcdR). While the sequence of TcdA, TcdE, TcdR, and TcdC are almost identical between historical and hypervirulent strains, TcdB is more variable (96% similarity, 92% identity). TcdB from a hypervirulent strain (TcdB$_{HV}$) has been found to be more potent on cultured cells than TcdB from a historical strain (TcdB$_{HIST}$). In line with this we also found that TcdB$_{HV}$ caused more extensive and broader tissue pathologies in a zebrafish embryo model. As a possible underlying mechanism for these differences in activity, it has been found previously that TcdB$_{HV}$ is translocated into cells more rapidly and is autoprocessed more efficiently than TcdB$_{HIST}$.

Interestingly, the greatest sequence variation between the two forms of TcdB is found in the C-terminal domain (CTD), which we define as the region of the toxin between amino acid 1651 and the terminal residue at position 2366. There is an overall 88% sequence identity between TcdB$_{HV}$1651-2366 and TcdB$_{HIST}$ 1651-2366. The CTD of TcdB encodes combined repetitive oligopeptides (CROPs), which are thought to be responsible for the recognition of glycans on target cells, and as such the CTD is often referred to as the receptor binding domain. However, the role of the CTD as the receptor binding domain is still very much debated as no receptor has been identified, and studies in TcdA have shown that this region contributes to, but is not required for cellular uptake of the toxin. The CTD is also antigenic and known to contain neutralizing epitopes. Yet, whether sequence differences in the CTD of TcdB$_{HV}$ and TcdB$_{HIST}$ alter the tropism or antigenic profiles of these two forms of the toxin is not known.

Upon examining the differences in the lethality and in vivo pathologies of TcdB$_{HV}$ and TcdB$_{HIST}$, the data indicates that TcdB$_{HV}$ exhibits a lethal dose substantially lower than TcdB$_{HIST}$. Additionally, while both toxins caused pronounced hemorrhaging in major organs, TcdB$_{HV}$ causes brain pathologies in vivo as well as an increased cytotoxicity on brain microvascular cells in vitro.

The use of *C. difficile* toxin as a vaccine has been tried by others, but has had limited success. Although the use of the vaccine results in the production of antibodies, this does not always correlate with protection against future *C. difficile* infection. Therefore, there is a need for a *C. difficile* vaccine that is capable of conferring protection against future infection.

BRIEF DESCRIPTION OF THE DRAWINGS

FIGS. 1A and 1B show the comparative survival curves of mice injected with TcdB$_{HIST}$ and TcdB$_{HV}$. Kaplan-Meier graphs show the time to death of BALB/c mice that were injected intravenously with TcdB. (A) Survival time of mice (n=4) injected with 1 ug, 500 ng, 100 ng, and 50 ng of TcdB$_{HIST}$. (B) Survival time of mice (n=4) injected with 200 ng, 100 ng, 50 ng, 25 ng, and 12.5 ng of TcdB$_{HV}$;

FIGS. 2A and 2B show the in vivo pathologies of TcdB$_{HIST}$ and TcdB$_{HV}$. (A) Top-Liver pathologies from BALB/c mice injected with (from left to right) 50 ng, 1000 ng, 500 ng, and 100 ng of TcdB$_{HIST}$. Bottom-Liver pathologies from BALB/c mice injected with (from left to right) 12.5 ng, 200 ng, 100 ng, or 50 ng of TcdB$_{HV}$. All photos are a 20× magnification of H&E stained sections and are listed by survival time. (B) Pathologies of the cerebrum and cerebellum with arrows pointing to areas of hemorrhaging. Representative photos (20×) of H&E stained sections from BALB/c mice injected with 100 ng TcdB$_{HIST}$ (top) or 50 ng of TcdB$_{HV}$ (bottom);

Figure 5:
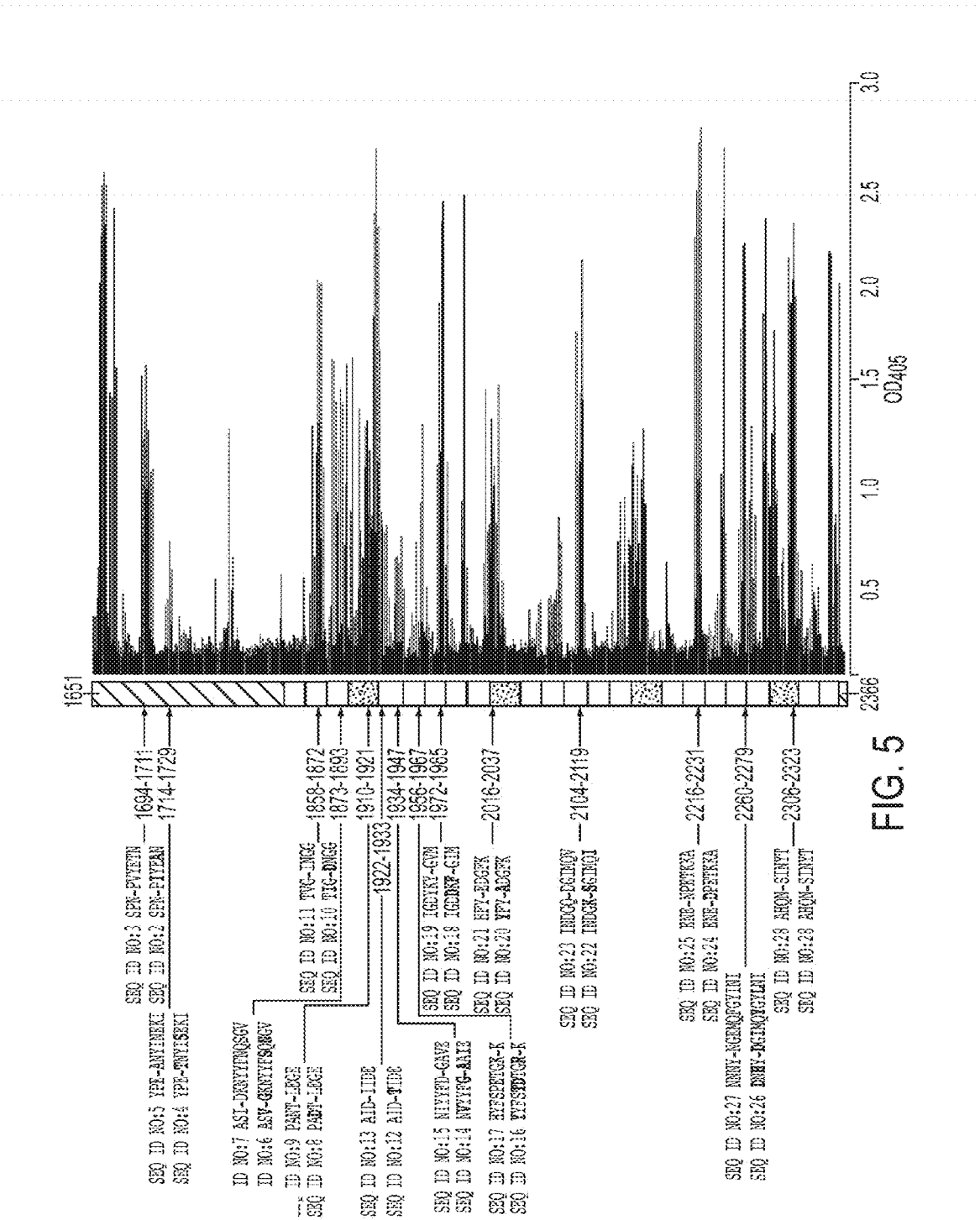
Figure 6A:
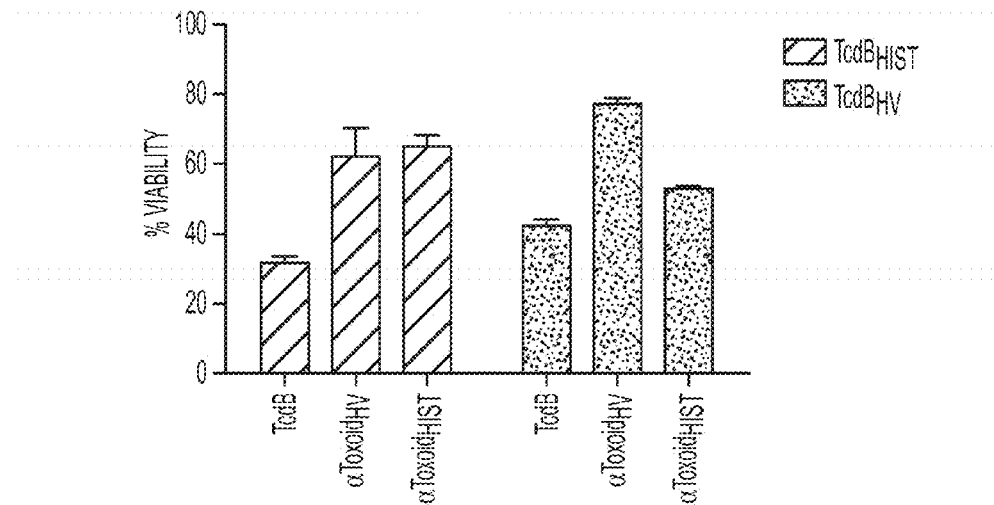
Figure 6B:
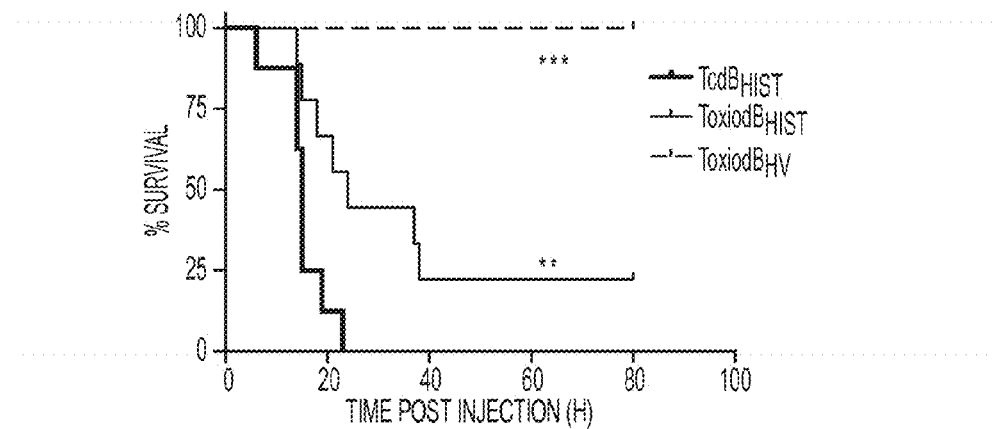
Figure 6C:
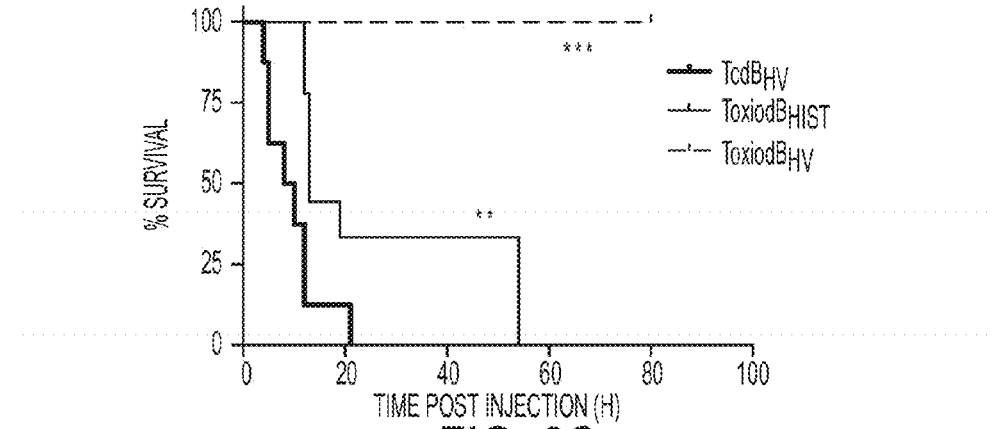

***p<0.001 (B) ELISA data showing the specificity of the αCTD antibodies to $TcdB_{HIST}$ and $TcdB_{HV}$ as measured by the optical density at 405 nm. (C) Percent viability of CHO cells treated for 24 hrs with $TcdB_{HIST}$ alone or combined with $αCTD_{HIST}$ antiserum, or with $αCTD_{HIST}$ antiserum plus excess of the $CTD_{HIST}$ or $CTD_{HV}$ protein fragments. Cell viability was determined by WST-8 staining and the error bars represent the standard deviation from the mean of three samples. (D) Representative phase contrast photographs of CHO cells after 6 h exposure to (a) 0.1 μg/ml of $TcdB_{HIST}$ alone or 0.1 μg/ml $TcdB_{HIST}$ with (b) 1:100 $CTD_{HIST}$ antiserum or 1:100 $CTD_{HIST}$ antiserum plus (c) excess $CTD_{HIST}$ or (d) $CTD_{HV}$ (e) untreated control;

FIG. 5 shows epitope mapping using synthetic peptide ELISAs (designated as SEQ ID NOS:2-28). Peptide ELISA of $αCTD_{HIST}$ (black) and $αCTD_{HV}$ (gray) anti-serum lined up against a representation of the TcdB CTD. The CTD is drawn from amino acid 1651 through 2366, and the white and filled boxes indicate the locations of the 24 CROP domains. The bars indicate the reactivity of the sera to overlapping peptide sequences from the CTD of $TcdB_{HIST}$. The arrows on the left indicate peaks of at least two consecutive bars with an OD over 0.5 that differed in reactivity or sequence coverage between $αCTD_{HIST}$ and $αCTD_{HV}$. The amino acid location of each epitope is indicated, as well as the sequence of the epitopes in $TcdB_{HIST}$ (top) and $TcdB_{HV}$ (bottom), with any sequence variation marked in bold;

FIGS. 6A to 6C show immunoprotection against TcdB in vivo and in vitro after immunization with $ToxoidB_{HV}$. (A) Percent viability of CHO cells treated for 24 hrs with $TcdB_{HIST}$ or $TcdB_{HV}$ alone or after preincubation for 30 minutes with $αToxoidB_{HIST}$ antiserum or $αToxoidB_{HV}$ antiserum. Cell viability was determined by WST-8 staining and the error bars represent the standard deviation from the mean of three samples. (B-C) Kaplan-Meier graphs showing the time to death of C57Bl/6 mice that were injected intravenously with a $2×LD_{100}$ of $TcdB_{HIST}$ (A) or $TcdB_{HV}$ (B) after immunization with $ToxoidB_{HIST}$ (red), $ToxoidB_{HV}$ (dashed), or control peptide (black) (n=9). Log-rank analysis performed using Prism, *p<0.001, p<0.01; and FIG. 7 shows the full length amino acid sequence of $TcdB_{HV}$ (SEQ ID NO:1) from a hypervirulent strain 027 of *C. difficile*.

DETAILED DESCRIPTION

Before describing various embodiments of the presently disclosed inventive concepts in more detail by way of exemplary description, examples, and results, it is to be understood that the presently disclosed inventive concepts are not limited in application to the details of methods and compositions as set forth in the following description. The presently disclosed inventive concepts are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the presently disclosed inventive concepts may be practiced without these specific details. In other instances, features which are well known to persons of ordinary skill in the art have not been described in detail to avoid unnecessary complication of the description.

Unless otherwise defined herein, scientific and technical terms used in connection with the presently disclosed inventive concepts shall have the meanings that are commonly understood by those having ordinary skill in the art. Further, unless otherwise required by context, singular terms shall include pluralities and plural terms shall include the singular. All patents, published patent applications, and non-patent publications mentioned in the specification are indicative of the level of skill of those skilled in the art to which the presently disclosed inventive concepts pertain.

All patents, published patent applications, and non-patent publications referenced in any portion of this application are herein expressly incorporated by reference in their entirety to the same extent as if each individual patent or publication was specifically and individually indicated to be incorporated by reference.

All of the compositions and methods of production and application thereof disclosed herein can be made and executed without undue experimentation in light of the present disclosure. While the compositions and methods of the presently disclosed inventive concepts have been described in terms of particular embodiments, it will be apparent to those of skill in the art that variations may be applied to the compositions and/or methods and in the steps or in the sequence of steps of the method described herein without departing from the concept, spirit and scope of the inventive concepts. All such similar substitutes and modifications apparent to those having ordinary skill in the art are deemed to be within the spirit and scope of the inventive concepts as defined herein.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the subjects.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species (e.g., a particular essential oil) is the predominant species present (i.e., on a molar basis it is more abundant than any other active agent in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. Most particularly, the object species may be purified to essential homogeneity (contaminant species cannot be detected in the composition by conventional detection methods) wherein the composition consists essentially of a single macromolecular species. The term "pure" or "substantially pure" also refers to preparations where the object species (e.g., the active agent) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal Non-limiting examples of animals within the scope and meaning of this term include guinea pigs, dogs, cats, rats, mice, horses, goats, cattle, sheep, zoo animals, monkeys, non-human primates, and humans.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" refer to a composition that may be administered to a subject by any method known in the art or otherwise contemplated herein, wherein administration of the composition brings about a therapeutic effect as described elsewhere herein. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. In addition, the compositions of the presently disclosed inventive concepts may be designed to provide delayed, controlled, extended, and/or sustained release using formulation techniques which are well known in the art. The term "topical" as used herein to define a mode of administration, means that a material is administered by being applied to the skin or internally to an epithelial tissue.

The term "effective amount" refers to an amount of a vaccine composition which is sufficient to exhibit a detectable therapeutic effect such as an immunity against *C. difficile*. The effective amount for a patient will depend upon the type of patient, the patient's size and health, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "cross-neutralizing response" refers to an immune response which is at least partially effective against both a hypervirulent strain of *C. difficile* and a heterologous or historical strain of *C. difficile*.

In certain embodiments, the presently described inventive concepts are directed to vaccine compositions useful in initiating an immune response against an organism of the genus *Clostridium* which comprise an immunogenic-effective amount of a toxin and/or a toxoid derived from the toxin of said organism in combination with a pharmaceutically acceptable carrier. In certain embodiments, the toxin is toxin B, is derived from a hypervirulent strain of *Clostridium difficile*, such as but not limited to hypervirulent strain ribotype 027, and is administered in the form of a toxoid formed from the toxin. The toxoid may be formed from the toxin in any appropriate manner known to persons having ordinary skill in the art. In at least one embodiment, the vaccine composition comprises a TcdB toxin or toxoid, wherein the TcdB toxin (or toxoid derived therefrom) is a natural toxin derived from a hypervirulent (HV) strain of *C. difficile*, such as the 027 ribotype or is a recombinantly-produced form of the toxin. In certain embodiments, the presently described inventive concepts are directed to the preparation of a TcdB toxoid from a TcdB toxin that can be used as a vaccine to promote the production of an antibody having protective properties against *C. difficile* infection or in treating a subject having an active *C. difficile* infection. In certain embodiments, the vaccine composition is effective against homologous and heterologous strains of *Clostridium difficile*.

The presently disclosed inventive concepts include a method for stimulating an organism's immune response against a *Clostridium* species, for example *C. difficile*, which comprises administering to said organism an immunogenic-effective amount of a toxin of *Clostridium* in combination with a pharmaceutically acceptable carrier. The immune response may include but is not limited to a cross-neutralizing response. At least one embodiment is a method of conferring immunity against a *C. difficile* infection comprising the steps of preparing a vaccine composition comprising a Tcd B toxoid, wherein the TcdB toxoid is produced from a TcdB toxin derived from a HV strain such as but not limited to ribotype 027 and introducing the vaccine composition into a subject. The subject may then be tested for immunity. The administration of the vaccine can be, but is not limited to, parenteral, subcutaneous, intramuscular, intraperitoneal or intravenous.

*C. difficile* infection (CDI) is a complex illness. It is well-established that *C. difficile* causes serious colonic inflammation through the actions of TcdA, and perhaps TcdB. The contribution of TcdB to inflammation of the colon is not clearly understood, but there do appear to be situations in which TcdB substitutes for TcdA in damaging the intestines. Although the intestinal inflammatory damage is a critical element of this disease, systemic complications may ultimately determine the fate of patients with severe forms of CDI. In fact, there is increasing evidence for systemic circulation of both TcdA and TcdB in this disease. Yet, very little is known about the underlying mechanisms of *C. difficile*-induced systemic damage and complications. Systemic damage is not a result of bacteremia, as blood cultures have been repeatedly shown to be sterile in *C. difficile* patients. Thus, the more reasonable explanation is that the toxins are released into the bloodstream of patients where they cause systemic damage. There are numerous observations supporting this idea. In recent work using a piglet model of *C. difficile* infection, TcdA and TcdB were detected in the bloodstream of the infected animals. Other work has demonstrated that serum IgG and not mucosal IgA against the toxins, correspond with protection against illness and relapse.

Despite the fact that TcdA and TcdB are well known to exhibit different tropisms, the underlying reasons for this difference are not known. However, just as there are differences in tissue tropism between TcdA and TcdB, our data suggests there are differences between the tropism of TcdB from different strains of *C. difficile*. Whether the CTD is the only region that accounts for these differences is not known, but data suggests that this domain is very likely to be involved with variations in interactions with target cells.

It is also important to consider this variation in the context of virulence of *C. difficile*, as well as vaccination. $TcdB_{HV}$ enters cells more rapidly and efficiently than $TcdB_{HIST}$ due to the fact that neutralizing epitopes of $TcdB_{HV}$ are sufficiently altered to avoid toxin neutralization or that the toxin has an entirely different mechanism of interacting with and entering the cell.

In at least one embodiment of the presently disclosed inventive concepts, the toxoid of $TcdB_{HV}$ is used to provide a vaccine that generates a broadly neutralizing response against *C. difficile* in vitro and in vivo. This is an unexpected result given that the CTD of $TcdB_{HV}$ was not subject to neutralization and past studies have found that TcdB toxoid is not a highly effective vaccine. It has been known for many years that anti-serum does not cross neutralize TcdA and TcdB, making it reasonable to consider the possibility that anti-serum to the variant forms of TcdB also do not cross neutralize. However, as shown herein this is not the case. As shown in FIG. 6, mice vaccinated with the $TcdB_{HV}$ were completely protected against both $TcdB_{HIST}$ and $TcdB_{HV}$. In other words, the $TcdB_{HV}$ vaccine was capable of conferring protection against the homologous strain of *C. difficile* from which the corresponding toxin/toxoid was derived, as well as against an unrelated heterologous strain of *C. difficile*. In line with a prior study, the toxoid of $TcdB_{HIST}$ evoked only marginal immunoprotection against TcdB, and we found this to be true for mice challenged with either the historical or hypervirulent form of the toxin. This raises the possibility that converting $TcdB_{HIST}$ into a toxoid alters the protein in a way that reduces immunogenicity, but sequence differences in $TcdB_{HV}$ make this form of the toxin more effective as a vaccine when it is a toxoid.

The differences in $TcdB_{HV}$ and $TcdB_{HIST}$ toxicity and antigenicity may also influence recurrence in CDI. Between 20%-25% of all CDI patients experience at least one bout of recurrence, and the first recurrence leads to a 40% chance of recurring a second time. Interestingly, over 50% of recurrences are caused by infection with a new strain of *C. difficile* and these cases are sometimes described as reinfection instead of recurrence or relapse. Thus, it is reasonable to suggest that variations in the antigenic make-up of TcdB could influence recurrence and reduce the likelihood of cross-strain immunoprotection. A neutralizing antibody response to $TcdB_{HIST}$ may not protect against recurrence caused by *C. difficile* NAP1/BI/027. In a similar vein, the differences in TcdB toxicity could influence recurrence. A recent study of nearly 1700 CDI patients found that patients experiencing severe disease and patients with higher levels of detectable toxins were more likely to experience recurrence. In line with this is a recent report showing that patients infected with a hypervirulent (NAP1/BI/027) *C. difficile* were more likely to experience recurrence. Collectively, these findings suggest the antigenic variations and differences in toxicity between $TcdB_{HIST}$ and $TcdB_{HV}$ could not only contribute to primary infection, but may be determinants in recurrent CDI.

Overall, these findings demonstrate differences between TcdB produced by historical and hypervirulent strains of *C. difficile*. The sequence variations in $TcdB_{HV}$ impact the toxin's cytotoxicity, lethality, and antigenic make-up and likely contribute to the overall heightened virulence of *C. difficile* NAP1/027/BI strains.

As noted, in at least one embodiment, the presently described inventive concepts include a method of conferring immunity to *C. difficile* infection comprising the steps of preparing a vaccine composition comprising a Tcd B toxoid, introducing the vaccine composition into a subject, which may be a test subject. The subject, including the test subject, may be tested for immunity. In at least one embodiment, the Tcd B toxoid is derived from the HV strain.

A further embodiment is directed to a method of conferring protection against *C. difficile* infection comprising administering to a subject in need thereof an effective amount of a vaccine comprising toxin B of *C. difficile*, wherein the administration of the vaccine confers immunity against infection by *C. difficile*. In at least one embodiment the toxin B is $TcdB_{HV}$ toxoid.

In other embodiments of the invention, the vaccine composition comprising the toxoid confers protection against multiple forms of the toxin.

As noted, in certain embodiments, the presently described inventive concepts are directed to vaccine compositions which comprise an immunogenic-effective amount of a *Clostridium difficile* toxin, such as toxin B derived from a hypervirulent strain of *Clostridium difficile* and is administered in the form of a toxoid. In at least one embodiment, the vaccine composition comprises a TcdB toxoid, wherein the TcdB toxoid is derived from a hypervirulent (HV) strain of the 027 ribotype. In certain embodiments, the presently described inventive concepts the toxoid may optionally be combined with pharmaceutically-acceptable carriers, diluents, and/or adjuvants, such as physiological saline solutions, and buffered saline solutions at neutral pH such as phosphate buffered saline (PBS). Other types of carriers include liposomes or polymers and the like. The pharmaceutically acceptable carrier, diluent, or adjuvant in the vaccine can be selected by standard criteria. By "pharmaceutically acceptable" is meant a material that is not biologically or otherwise undesirable, i.e., the material may be administered to an individual along with the selected compound without causing any undesirable biological effects or interacting in a undesirable manner with any of the other components of the pharmaceutical composition in which it is contained. The carrier, diluent, or adjuvant may depend on the method of administration and the particular patient.

Non-limiting examples of adjuvants which may be used include Freund's incomplete adjuvant, Freund's Complete adjuvant, alum, monophosphoryl lipid A, alum phosphate or hydroxide, QS-21, salts, i.e., $AlK(SO_4)_2$, $AlNa(SO_4)_2$, $AlNH_4(SO_4)_2$, silica, kaolin, muramyl dipeptide, carbon polynucleotides, i.e., poly IC and poly AU, and QuilA and Alhydrogel and the like. Optionally, the toxoid can be combined with immunomodulators and immunostimulants. The vaccine may comprise microparticles such as liposomes or ISCOMs.

Generation of a protective immune response by the vaccine can be measured by the development of antibodies. The amounts of the toxoid described herein that can form a protective immune response typically are in a unit dosage form of about 0.001 μg to 100 mg per kg of body weight, more preferably 0.01 μg to 1 mg/kg of body weight, and more preferably about 0.1 μg to about 10 μg/kg body weight, for example, at an interval of about 1 to 6 weeks intervals between immunizations.

The vaccine compositions are administered to animals which may become infected by the disease organism described herein, including but not limited to dogs, cats, rabbits, rodents, horses, livestock (e.g., cattle, sheep, goats, and pigs), zoo animals, ungulates, primates, and humans.

The vaccine compositions may be made from an antigenic fragment of a TcdB toxoid described herein, wherein such fragment is large enough to stimulate a protective immune response, including but not limited to a cross-neutralizing response, in accordance with the presently disclosed inventive concepts. For example, the fragment may comprise a minimum length of 10, 25, 50, 75, 100, 125, 150, 175, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, or 2350 or more amino acids of the TcdB toxoid.

The vaccines described herein are also useful to generate neutralizing antibodies which can be used as a passive immune serum to treat or ameliorate the symptoms in patients. A vaccine composition as described above could be administered to an animal such as a horse or a human until a neutralizing antibody response is generated. These neutralizing antibodies can then be harvested, purified, and utilized to treat patients exhibiting symptoms.

The neutralizing antibodies are administered to patients exhibiting disease symptoms in an amount effective to neutralize the effect of the pathogen. The neutralizing antibodies can be administered intravenously, intramuscularly, intradermally, subcutaneously, and the like. In one embodiment of the treatment method, the neutralizing antibody can be administered in conjunction with antibiotic therapy. The amount of neutralizing antibodies typically administered is about 1 mg of antibody to 1000 mg/kg, more preferably about 50-200 mg/kg of body weight.

The vaccine composition is preferably prepared as a pharmaceutical composition containing an immunoprotective, non-toxic amount of the toxoid in a non toxic and sterile pharmaceutically acceptable carrier.

The vaccines of the presently disclosed inventive concepts can be administered to the appropriate subject in any manner known in the art, e.g., orally intramuscularly, intravenously, sublingual mucosal, intraarterially, intrathecally, intradermally, intraperitoneally, intranasally, intrapulmonarily, intraocularly, intravaginally, intrarectally or subcutaneously. They can be introduced into the gastrointestinal tract or the respiratory tract, e.g., by inhalation of a solution or powder containing the conjugates. In some embodiments, the compositions can be administered via absorption via a skin patch. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained.

A vaccine composition is administered in an amount sufficient to elicit production of antibodies as part of an immunogenic response. Dosage for any given patient depends upon many factors, including the patient's size, general health, sex, body surface area, age, the particular compound to be administered, time and route of administration, and other drugs being administered concurrently. Determination of optimal dosage is well within the abilities of a pharmacologist of ordinary skill.

The therapeutically effective and non-toxic dose of the vaccine can be determined by a person of ordinary skill in the art. However the specific dose for any person will depend upon a variety of factors including age, general health, diet of the patient, time and route of administration, synergistic effects with other drugs being administered and whether the vaccine is administered repeatedly. If necessary the vaccine will be administered repeatedly with one to three month intervals between each dose and with an optional booster dose later in time. Actual methods of preparing the appropriate dosage forms are known, or will be apparent, to those skilled in this art; for example, see Remington's Pharmaceutical Sciences, latest edition.

EXAMPLES

The presently disclosed inventive concepts, having now been generally described, will be more readily understood by reference to the following examples and embodiments, which are included merely for purposes of illustration of certain aspects and embodiments of the presently disclosed inventive concepts, and are not intended to be limiting. The following detailed examples and methods describe how to make and use the various vaccine compositions of the presently disclosed inventive concepts and are to be construed, as noted above, only as illustrative, and not limitations of the disclosure in any way whatsoever. Those skilled in the art will promptly recognize appropriate variations from the compositions and procedures.

Animals, Bacterial Strains, and Cell Culture

C. difficile VPI 10463 (produces TcdB with identical sequence to the 630 strain) and C. difficile ribotype 027 were used as sources from which the two toxins, $TcdB_{HIST}$ and $TcdB_{HV}$, respectively, were purified. $TcdB_{HV}$ has the amino acid sequence SEQ ID No.1 (FIG. 7).

Female BALB/cJ and C57B/6J mice (Jackson Laboratories), aged 8 weeks, were purchased from The Jackson Laboratories (Bar Harbor, Me.) and handled in accordance with IACUC guidelines at University of Oklahoma Health Science Center.

Rat Brain Microvascular Endothelial Cells (RBMVEC) and Rat Aortic Endothelial Cells were a generous gift from the laboratory of Dr. Eric Howard (University of Oklahoma Health Sciences Center) and have been described previously. CHO cells were purchased from American Type Culture Collection (ATCC). RBMVEC and RAEC were grown in DMEM containing 10% FBS while CHO cells were grown in F12-K with 10% FBS. All cell types were used between passage 15-30, and were maintained in tissue culture treated T-75 flasks (Corning) at 37° C. in the presence of 6% $CO_2$.

Production of Native Toxin, Toxoid Preparation, and Purification of Recombinant TcdB Fragments C. difficile was cultured using the dialysis method as previously described and TcdB was isolated by consecutive steps of thyroglobulin affinity chromatography to remove TcdA followed by anion-exchange (Q-Sepharose) and high-resolution anion-exchange (Mono-Q) chromatography in 20 mM Tris-HCl, 20 mM $CaCl_2$, pH 8.0. Purification steps were followed by protein determination using the Bradford method, visualization of a single 270 kDa band by SDS-PAGE, and LC/MS/MS analysis (University of Oklahoma Health Science Center) to confirm protein identity.

Toxoid versions of $TcdB_{HIST}$ and $TcdB_{HV}$ were prepared by mixing 500 μl of TcdB (0.4 μg/μl) into 500 μl of 8% formaldehyde with 8.5 mg of lysine to help prevent precipitation and aggregation of the formalinized protein, and incubating at 37° C. overnight. The volume was then brought up to 10 ml with PBS, yielding 20 μg/ml of ToxoidB in 0.4% formaldehyde with 0.425 mg/ml lysine. Both toxoid preparations lacked toxic activity as confirmed by the absence of cytopathic effects on CHO cells.

The CTD-encoding region of tcdb gene (nucleotides 4935-7111) from the strain VPI 10463 was codon optimized and cloned into pET15b (Genscript). The CTD of the tcdb gene (nucleotides 4935-7111) from the NAP1 strain was cloned from a pET15b plasmid containing full-length tcdb that had been codon optimized by Genscript. The CTD gene was amplified using primers 5'-GATCATATGCTGTAT-GTGGGTAACCG-3' (SEQ ID No. 29) and 5'-AACG-GATCCTTATTCGCTAATAACCA-3' (SEQ ID No. 30) containing BamHI and Nde1 sites for cloning into pET15b. The CTDs were expressed using Escherichia coli BL21 star DE3 (Invitrogen) at 16° C. overnight and then purified by $Ni^{2+}$ affinity chromatography (HisTrap, GE Life Sciences) resulting in proteins representing $TcdB_{1645-2366}$ from both $TcdB_{HIST}$ and $TcdB_{HV}$.

Lethal Dose Determination and Organ Pathologies

To determine the differences in the minimum lethal dose of $TcdB_{HIST}$ and $TcdB_{HV}$, 100 μl of $TcdB_{HIST}$ or $TcdB_{HV}$ dilutions in phosphate-buffered saline was injected intravenously into the tails of BALB/cJ mice using a 27-gauge needle. Twenty mice were given $TcdB_{HIST}$ in groups of 4, receiving doses of 2 μg, 1 μg, 500 ng, 100 ng, and 50 ng. Twenty additional mice were injected with doses of 200 ng, 100 ng, 50 ng, 25 ng, and 12.5 ng of $TcdB_{HV}$ (n=4). The animals were monitored for up to 7 days post challenge for toxin effects and mortality, and mice were euthanized if they became significantly distressed or moribund. Survival was graphed using Kaplan-Meier analyses on GraphPad Prism (GraphPad Software, Inc., La Jolla, Calif.).

Immediately after death, the mice were dissected and major organs and tissues were submerged in formalin fixative overnight. Tissue sectioning, slide preparation, H&E staining, and pathology analysis was performed by the Department of Comparative Medicine at OUHSC.

Animal Immunizations and TcdB Challenges

Rabbits were immunized with 0.1 mg of the CTD fragment of TcdB in complete Freund's adjuvant on day 1 and boosted with 0.1 mg in incomplete Freund's adjuvant on days 14, 21, and 49. Blood samples were collected on days 0, 35, and 56. These experiments were carried out by Cocalico Biologicals Inc. (Reamstown, Pa.).

BALB/cJ mice (20 mice each for $ToxoidB_{HIST}$ and $ToxoidB_{HV}$) were injected in equal portions subcutaneously and intraperitoneally with 2 μg of toxoid in PBS emulsified 1:1 in 100 μl of complete Freund's adjuvant on day 1 and boosted with 2 μg in incomplete Freund's adjuvant on day 10. Control mice were similarly immunized and boosted using an unrelated peptide. Blood samples were collected via tail bleeds on day 0 and 24, and each bleed tested by ELISA to evaluate toxoid response.

After completion of the immunizations, the mice were subjected to i.v. challenges of $TcdB_{HIST}$ and $TcdB_{HV}$. Each immunization group ($ToxoidB_{HIST}$, $ToxoidB_{HV}$, control) contained 20 mice, and 9 from each group were injected via the tail vein with a 2-fold lethal dose of either $TcdB_{HIST}$ or $TcdB_{HV}$. The previously established minimum lethal dose was used to set the $2 \times LD_{100}$ at 200 ng per mouse for $TcdB_{HIST}$ and 50 ng per mouse for $TcdB_{HV}$. The remaining 2 mice from each group were euthanized and exsanguinated for serum collection. The animals were monitored for up to 7 days post challenge for toxic effects and mortality, and mice were euthanized if they became significantly distressed or moribund. Survival was graphed using Kaplan-Meier analyses and compared with the Log-rank test on GraphPad Prism (GraphPad Software, Inc., La Jolla, Calif.).

Characterization of Antibody Responses

Direct antigen ELISAs were used to measure the antibody reactivity in animal sera. One microgram of purified TcdB or CTD fragment was coated per well in polystyrene plates at 4° C. overnight. The plates were washed and blocked with 0.1% BSA in PBS for 1 h at room temperature. Then, the rabbit sera diluted at 1:100 and 1:1000 in PBS-Tween with 0.1% BSA was added in triplicate and incubated for 2-3 h at room temperature. Plates were washed with PBS-Tween and incubated with anti-rabbit IgG conjugated to alkaline phosphatase (Jackson ImmunoResearch Laboratories, Inc) at a dilution of 1:5,000 for 3 hours at room temperature then washed and developed with p-Nitrophenyl Phosphate substrate (Sigma). Plates were read at 405 nm using a Tecan infinite plate reader (Tecan Group, Ltd.). Plates were read when the positive control reached an OD of 1.0 and the assay was considered invalid if the negative control was over OD 0.2.

Cytotoxicity and TcdB Neutralization Assays

Cells were seeded in 96 well plates at a density of $1-2 \times 10^4$ cells per well in DMEM or F12-K (ATCC) containing 10% FBS (ATCC). For TcdB sensitivity measurements on endothelial cells, dilutions of $TcdB_{HIST}$ or $TcdB_{HV}$ were added to each well in triplicate, and the cells were incubated 24 h and cell viability was measured by CCK-8 (Sigma). In order to measure neutralization of TcdB, a 1:10 dilution of serum raised in rabbits against the CTD or mouse serum to the toxoid was preincubated with $TcdB_{HIST}$ or $TcdB_{HV}$ for 1 h at 37° C. in F12-K media (ATCC). CHO cells were treated with the toxin/antiserum mixture or toxin alone and incubated at 37° C. for up to 24 h. Cells were analyzed under the microscope for cell rounding at 2-4 h and cell viability was measured at 24 h using a CCK-8 assay according to manufacturers instructions (Sigma).

Fine Specificity Epitope Mapping with Solid-Phase Peptide ELISAs

The 358 decapeptides overlapping by 8 amino acids covering the length of the CTD region from $TcdB_{HIST}$, were covalently synthesized on polyethylene pins as previously described and used to assay antibody specificity with a modified ELISA assay. Blocking was done in 3% milk in PBS for 1 h at room temperature, then the pins were incubated in 100 μl/well of sera diluted 1:100 in 3% milk-PBS with 0.05% Tween for 2 h at room temperature. The pins were washed 4 times for 8 min with mild agitation in PBS-Tween and then incubated with 100 μl/well of a 1:5,000 dilution of anti-rabbit IgG conjugated to alkaline phosphatase in 3% milk-PBS with 0.05% Tween at 4° C. overnight. (Jackson ImmunoResearch Laboratories). Next, washes were performed as before and the pin ELISA was developed using 100 μl/well of a 1 mg/ml solution of p-nitrophenyl phosphate dissolved in 150 mM carbonate buffer pH 10.4 containing 100 mM glycine, 1 mM $MgCl_2$ and 1 mM $ZnCl_2$. The absorbance was read at 405 nm using a Tecan infinite plate reader (Tecan Group, Ltd.), and the results were normalized with to the standard positive control peptide having an OD of 1.0. Positive epitopes were defined as at least two consecutive peptides with an OD greater than 2 standard deviations above the mean of normal serum.

$TcdB_{HV}$ Exhibits a Lower Lethal Dose than $TcdB_{HIST}$

In previous work we found that that $TcdB_{HV}$ is more cytotoxic and causes broader tissue damage in a zebrafish embryo model than $TcdB_{HIST}$; however, how this relates to lethal doses is not known. In the first set of experiments in this study we determined and compared the lethal doses of $TcdB_{HIST}$ and $TcdB_{HV}$ in a murine systemic intoxication model. The previously published lethal dose of 220 μg/kg (i.p.) for $TcdB_{HIST}$ was used to establish a range of toxin concentrations for these treatments, but the lethality we observed via i.v. injection was much higher than previously reported. As a result, the initial doses of 2 μg (data not shown), 1 μg, and 500 ng of $TcdB_{HIST}$ were much more potent than anticipated, and resulted in a very rapid time to death (FIG. 1A). Therefore, the remaining mice were subjected to much lower doses of 100 ng and 50 ng of $TcdB_{HIST}$. Based on the results of the $TcdB_{HIST}$ treated mice, the $TcdB_{HV}$ group started with a dose of 200 ng and was continued with 1:2 dilutions down to 12.5 ng of $TcdB_{HV}$. After the mice were injected with $TcdB_{HIST}$ or $TcdB_{HV}$, they were followed for up to 7 days and the survival curves of the data from these experiments are shown in FIG. 1B.

The data shown in FIG. 1 indicate mice injected with $TcdB_{HV}$ succumb to the toxin at a lower dose than that observed in mice injected with $TcdB_{HIST}$. Within 24 h of treatment all of the mice administered 100 ng of $TcdB_{HV}$ died or reached a severe moribund condition. In comparison, mice administered the same dose of $TcdB_{HIST}$ did not succumb to the toxin until after 40 h and as long as 57 h. At the next lower dose (50 ng), no mice survived $TcdB_{HV}$ treatment, while all of the mice treated with $TcdB_{HIST}$ survived. Based on these outcomes, it is estimated that the $LD_{50}$ of $TcdB_{HV}$ to be between 625 ng/kg and 1.25 μg/kg body weight. In comparison, a higher range for $TcdB_{HIST}$ was estimated and fell between 2.5 μg/kg and 5 μg/kg body weight. The dose-related time to death was the most striking difference between to the two groups. For example, mice treated with 200 ng of $TcdB_{HIST}$ survived as long as 60 h, while mice treated with an identical dose of $TcdB_{HV}$ all succumbed to the toxin by 24 h. Thus, in line with previous studies demonstrating more potent effects on cultured cells and zebrafish embryos, $TcdB_{HV}$ also appears to be more toxic than $TcdB_{HIST}$ in a rodent model of intoxication.

$TcdB_{HV}$, But Not $TcdB_{HIST}$ Causes Extensive Brain Hemorrhaging

The results shown in FIG. 1, combined with our earlier findings in the zebrafish model, all point to the fact that $TcdB_{HV}$ is more toxic than $TcdB_{HIST}$. Recent work has detected TcdA and TcdB circulating in the bloodstream of piglets infected by *C. difficile*, and this correlated with systemic effects that could be blocked by passive administration of antibodies against the toxins. This led us to question whether $TcdB_{HV}$ might also cause more extensive systemic damage than $TcdB_{HIST}$ due to its higher potency. To assess this, mice were administered $TcdB_{HIST}$ (50 ng to 1000 ng) or $TcdB_{HV}$ (12.5 ng to 200 ng) and tissue pathologies were determined. Examination of tissues and organs from mice administered sublethal doses of the toxins did not reveal pathologies that differed from that of control (FIG. 2A). In contrast, tissue pathologies were found in several of the major organs examined from mice intoxicated with lethal doses of TcdB. Mice treated with either $TcdB_{HIST}$ or $TcdB_{HV}$ showed pronounced liver damage with extensive blood-pooling, parenchymal cell loss, and evidence of hemorrhage (FIG. 2A). To a lesser extent acute hepatocellular coagulative necrosis was observed, and the spleen also showed signs of hemorrhage along with follicular necrosis and possible apoptotic cells (data not shown). Additionally, the severity of all of the observed pathologies was more related to the length of time of toxin exposure rather than toxin concentration. FIG. 2A shows representative liver sections from $TcdB_{HIST}$ and $TcdB_{HV}$ treated mice, illustrating that the damage is the most extensive in mice receiving the minimum lethal dose and surviving for the longest period of time.

Despite the difference in lethality, the majority of the in vivo effects of $TcdB_{HIST}$ and $TcdB_{HV}$ were identical, with the exception of the moderate to severe hemorrhaging detected in the brain of $TcdB_{HV}$-treated mice. Indeed, brain hemorrhage was the most obvious difference between mice injected with the two forms of TcdB. The brains of mice treated with $TcdB_{HIST}$ displayed only small lesions while the brain hemorrhaging of $TcdB_{HV}$-treated mice was profuse with large multi-focal areas of blood accumulation within the cerebellum and cerebrum (FIG. 2B). These data suggest there may be a loss of endothelial integrity in mice challenged with TcdB, as well as a significant difference in the in vivo targeting and tropism of $TcdB_{HIST}$ versus $TcdB_{HV}$.

$TcdB_{HV}$ is Highly Toxic to Brain Microvascular Endothelial Cells

Figure 3A:
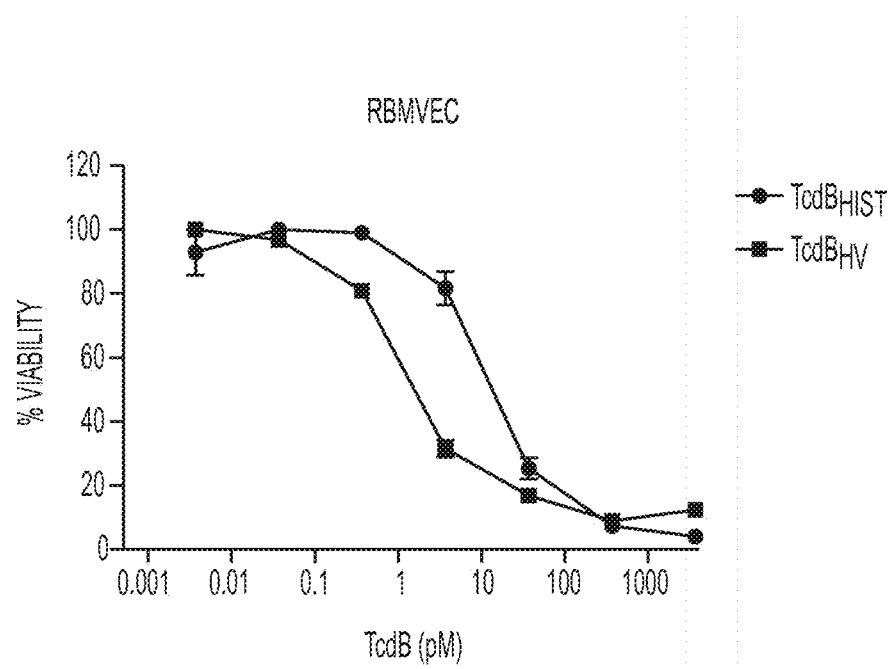
FIGS. 3A and 3B show the in vitro cytotoxicity of TcdB$_{HIST}$ and TcdB$_{HV}$ on endothelial cells. Rat aortic endothilial cells (A) or rat brain microvascular endothelial cells (B) were exposed to 10-fold dilutions of TcdB$_{HIST}$ (●) or TcdB$_{HV}$ (■) from 3.7 nM to 3.7 fM for 24 h and cell viability was determined by WST-8 staining. The error bars represent the standard deviation from the mean of at least three independent experiments containing three replicates.
Figure 3B:
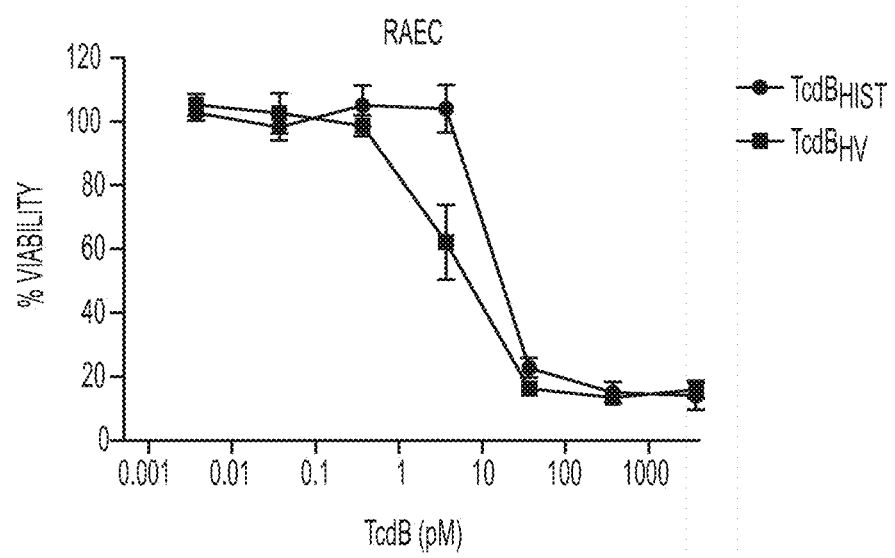

Experiments were next performed to determine the toxicity of the two forms of the TcdB on endothelial cell lines as a possible correlation with the differences in brain hemorrhaging. We first wanted to determine whether endothelial cells displayed increased sensitivity to TcdB compared to the epithelial cells (e.g. CHO cells) that are normally used in cytotoxicity assays. Rat Aortic Endothelial Cells (RAEC) exposed to $TcdB_{HIST}$ and $TcdB_{HV}$ displayed slight differences in cytotoxic effects (FIG. 3A). The $TCD_{50}$ dose for $TcdB_{HIST}$ of $1.41 \times 10^{-11}$ M was comparable to previously published observations of $TcdB_{HIST}$ toxicity on CHO cells of $2.53 \times 10^{-11}$ M while the $TCD_{50}$ dose for $TcdB_{HV}$ of $4.04 \times 10^{-12}$ was higher than the $TCD_{50}$ of $2.37 \times 10^{-13}$ for CHO cells. Since the major differences in pathology between $TcdB_{HIST}$ and $TcdB_{HV}$ occurred in the brain, we next tested Rat brain microvascular endothelial cells (RBMVEC) for differences in sensitivity to the two forms of TcdB. Interestingly, there was a significant difference in the cytotoxicity of TcdB$_{HV}$ on the RBMVECs, with the TCD$_{50}$ being 1.21× 10$^{-13}$ M compared to the TCD$_{50}$ of 1.34×10$^{-11}$ M for TcdB$_{HIST}$ (FIG. 3B). These data indicate TcdB causes cytopathic and cytotoxic effects on endothelial cells, and that RBMVECs have an increased susceptibility to TcdB$_{HV}$.

Differential Contributions of the Carboxy-Terminal Domains (CTD$_{HIST}$ and CTD$_{HV}$) to Cell Interactions and their Susceptibility to Antibody Neutralizations To further study the differences in the cell and organ targeting between TcdB$_{HIST}$ and TcdB$_{HV}$, we focused on the CTD, which is thought to be important in facilitating cell interactions. We hypothesized that if this region is indeed important in cell targeting, then the sequence differences between TcdB$_{HIST}$ and TcdB$_{HV}$ in this region could be an important factor in the distinct cell tropism and animal pathologies between the toxins. We also predicted that these differences could change the profile of antigenic epitopes, and perhaps neutralizing epitopes, in the CTD. We designed a set of experiments to address both of these possibilities.

In order to evaluate differences in the CTD of TcdB$_{HIST}$ and TcdB$_{HV}$ we expressed and purified protein fragments representing this region of each toxin. These fragments consisted of the final 721 amino acids of the TcdB protein, including the CROP region along with approximately 206 residues amino terminal to the CROP region. Based on previous sequence comparisons, there are 89 residues that differ between CTD$_{HIST}$ and CTD$_{HV}$.

Figure 4A:
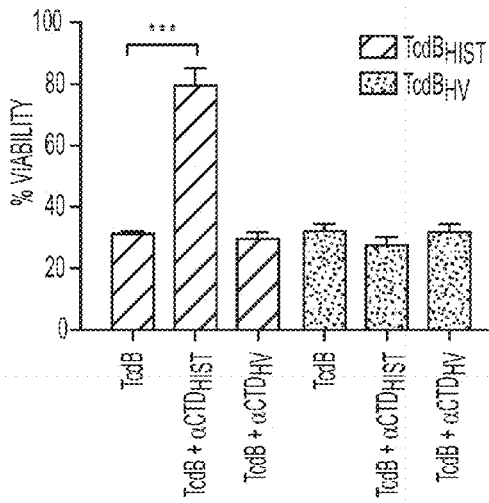
FIGS. 4A to 4D show the neutralization of TcdB with αCTD antiserum. (A) Percent viability of CHO cells treated for 24 hrs with TcdB$_{HIST}$ or TcdB$_{HV}$ alone or after preincubation for 30 minutes with αCTD$_{HIST}$ antiserum or αCTD$_{HV}$ antiserum. Cell viability was determined by WST-8 staining and the error bars represent the standard deviation from the mean of 2 independent experiments of three samples.
Figure 4B:
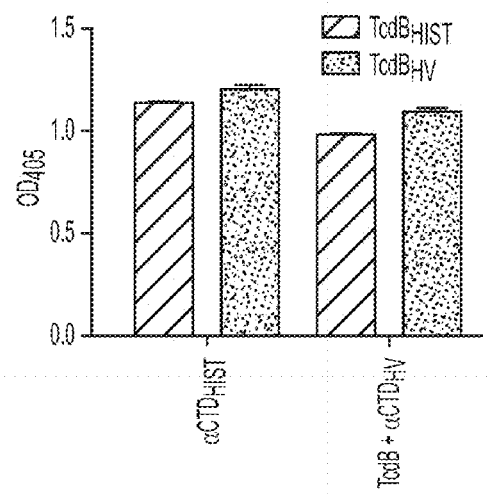
Figure 4C:
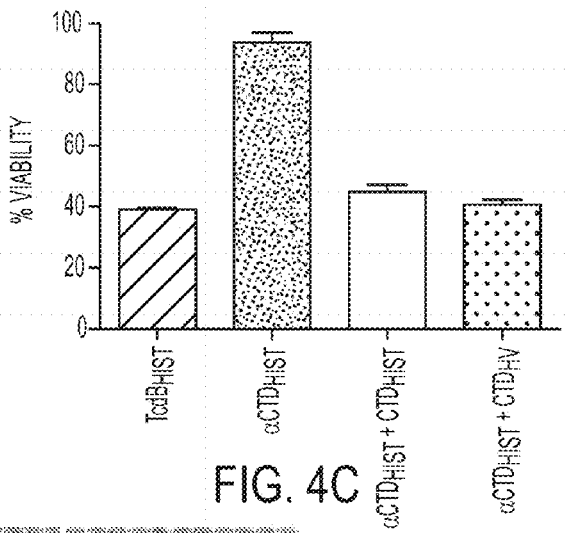

Initially, each CTD was used as an antigen to immunize rabbits for the collection of CTD antisera, which was then used in TcdB neutralization assays to further determine the impact of the CTD on the activity of both TcdB$_{HIST}$ and TcdB$_{HV}$. We first investigated the impact of αCTD$_{HIST}$ on the cytotoxicity of both TcdB$_{HIST}$ and TcdB$_{HV}$ and found that treatment with αCTD$_{HIST}$ neutralized the cytotoxic and cytopathic effects of TcdB$_{HIST}$ (FIG. 4A). However, αCTD$_{HIST}$ caused no detectable reduction in the cytotoxicity of TcdB$_{HV}$ (FIG. 4A). ELISA analysis confirmed that while αCTD$_{HIST}$ was only able to neutralize TcdB$_{HIST}$ in cell culture, the polyclonal sera could recognize both TcdB$_{HIST}$ and TcdB$_{HV}$ in vitro (FIG. 4C).

The observation that αCTD$_{HIST}$ was not able to cross-neutralize despite retaining the capacity to bind and recognize both TcdB$_{HIST}$ and TcdB$_{HV}$, led us to question whether the role of the CTD is altered in TcdB$_{HV}$. We predicted two possible explanations for the results we observed. First, the CTD of TcdB$_{HV}$ may not hold the same function and importance as the CTD of TcdB$_{HIST}$. Alternatively, if the CTD does play a fundamental role, the epitopes and regions responsible could be changed so that the critical residues escape recognition by the αCTD$_{HIST}$ serum. If the latter is the case, then it stands to reason that sera raised against the CTD of TcdB$_{HV}$ would recognize these changed epitopes and elicit a neutralizing response. When the αCTD$_{HV}$ antibody was used in the neutralization assay, we found that it elicited no protective response against either TcdB$_{HIST}$ or TcdB$_{HV}$ despite being able to recognize both forms of the toxin by ELISA (FIGS. 4B and 4C).

Figure 4D:
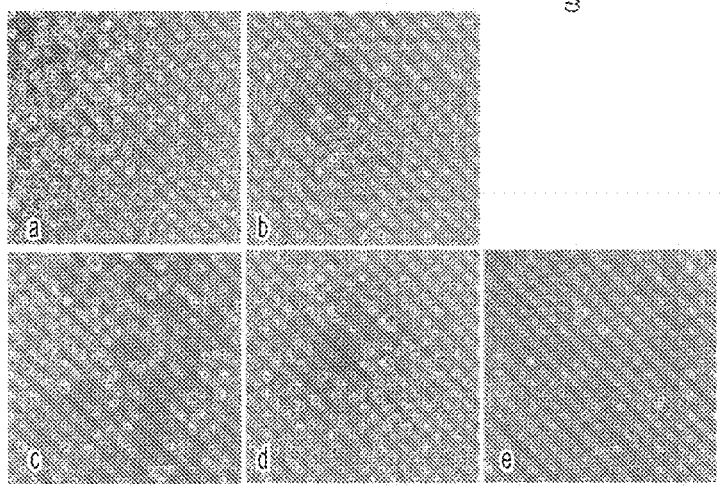

Because we found αCTD$_{HIST}$ serum could recognize TcdB$_{HV}$ by ELISA, our next experiments were to determine whether this interaction had any inhibitory effect in the neutralization assay. First, serum against αCTD$_{HIST}$ was preincubated with a 100-fold excess of CTD$_{HIST}$ or CTD$_{HV}$, before adding TcdB$_{HIST}$ and adding the mixture to CHO cells. The preincubation step allowed for the sera to interact with the CTD protein first, and potentially block binding of the antibodies to full length TcdB. As expected, the addition of CTD$_{HIST}$ in the neutralization assay results in the inhibition of antibody activity and a return to full cytotoxicity of TcdB$_{HIST}$ (FIGS. 4D and 4E). Surprisingly, preincubation with CTD$_{HV}$ yields the same result (FIGS. 4D and 4E)). This finding suggested that CTD$_{HV}$ contained epitopes that are neutralizing in CTD$_{HIST}$.

Fine Specificity Mapping of Antibody Responses Reveals Unique Epitopes Between TcdB$_{HIST}$ and TcdB$_{HV}$ In order to identify precise differences in epitopes between TcdB$_{HV}$ and TcdB$_{HIST}$ we used solid phase ELISA to map specific regions of antigenic variability. In all, 358 decamer peptides, overlapping by 8 residues and covering the entire CTD$_{HIST}$ sequence, were synthesized and tested for reactivity to CTD$_{HIST}$ and CTD$_{HV}$ sera. When we compared the peptides recognized by αCTD$_{HIST}$ to those recognized by αCTD$_{HV}$ we found an overall difference in the pattern of peptides recognized by the two antisera (FIG. 5). The analysis identified approximately 14 regions that were unrecognized or displayed reduced reactivity by the αCTD$_{HV}$ sera. The majority of the peptides identified are localized in the CROP domains toward the beginning and end of the CTD. Additionally, most of the epitopes that differ in recognition between αCTD$_{HIST}$ and αCTDHV are located sequentially, within the first seven repeats of the CTD. As summarized in FIG. 5, three peptides differed by just one amino acid, four peptides differed by two amino acids, two peptides differed by three amino acids, three peptides differed by four amino acids, and one peptide differed by five amino acids. We also identified a region that showed reduced peptide recognition by αCTD$_{HV}$ yet had no sequence variation, as well as several peptide regions that were recognized by αCTD$_{HV}$ alone (FIG. 5). These data suggest that sequence variation of TcdB$_{HV}$ impacts antibody recognition of linear epitopes and may contribute to differences in conformational epitopes as well.

Mouse Antiserum Against ToxoidB$_{HV}$ is Cross-Protective In Vitro and In Vivo

The observation that the CTD of TcdB$_{HV}$ is a poor target for the production of neutralizing antibodies raised concerns about the overall antigenicity of TcdB$_{HV}$. The majority of the amino acid sequence variation between TcdB$_{HIST}$ and TcdB$_{HV}$ occurs in the CTD, so we reasoned that producing antibodies using the holotoxin as an antigen could have better potential to be broadly neutralizing. Both TcdB$_{HIST}$ and TcdB$_{HV}$ were inactivated using formaldehyde to create ToxoidB$_{HIST}$ and ToxoidB$_{HV}$. These toxoids were used as antigens to immunize mice and test for protective antibodies against TcdB. After two subsequent boosts, serum was collected from the mice, and the neutralizing effects were tested in vitro. The data in FIG. 6A shows that the mouse antiserum toward ToxoidB$_{HV}$ protected against the cytotoxic effects of both TcdB$_{HIST}$ and TcdB$_{HV}$, while anti-Toxoid$_{HIST}$ was not cross-neutralizing, and only maintained the cell viability of the CHO cells treated with TcdB$_{HIST}$. The immunized mice were next tested for protection from TcdB in vivo, using a 2-fold minimum lethal dose of TcdB$_{HIST}$ or TcdB$_{HV}$. Consistent with the in vitro neutralization data, all mice immunized with ToxoidB$_{HV}$ were completely protected from i.v. challenge of both TcdB$_{HIST}$ and TcdB$_{HV}$ (FIGS. 6B and 6C), i.e., the TcdB$_{HV}$ vaccine was capable of conferring protection (cross-neutralizing) against the homologous strain of C. difficile from which the corresponding toxin/toxoid was derived, as well as against an unrelated heterologous strain of C. difficile. Immunization with ToxoidB$_{HIST}$ provided only a slight, yet significant protective effect, increasing the median survival from 15 h to 24 h in mice injected with TcdB$_{HIST}$, but only from 9 h to 13 h in mice challenged with TcdB$_{HV}$ (FIGS. 6B and 6C). Eventually, all of the ToxoidB$_{HIST}$ mice succumbed to the effects of TcdB$_{HV}$, and only two ToxoidB$_{HIST}$ mice were fully protected from TcdB$_{HIST}$ (FIGS. 6B and 6C). Whereas the antisera to the CTD of TcdB$_{HV}$ showed no effect, antibodies to the toxoid form of TcdB$_{HV}$ successfully inhibited toxicity, indicating that there can be a protective effect against TcdB$_{HV}$, and the important targets may be outside the CTD. In addition to the protective properties against *C. difficile* infection, the toxoid form of TcdB$_{HV}$ also demonstrates protection against multiple forms of the toxin.

In at least one embodiment, the presently disclosed inventive concepts are directed to a vaccine composition useful in initiating an immune response against *Clostridium difficile*. The composition, in this embodiment, includes an immunogenic-effective amount of at least one of (a) a toxin derived from a hypervirulent strain of *Clostridium difficile*, (b) a toxoid derived from said toxin, and (c) an immunogenic fragment of said toxin or said toxoid, and a pharmaceutically acceptable carrier, wherein the immune response initiated by the vaccine composition is effective against the hypervirulent strain and at least one heterologous strain of *Clostridium difficile*. The hypervirulent strain may be ribotype 027. The toxin may be toxin B and may be expressed from a recombinant source. The toxin may comprise SEQ ID NO: 1 or an immunogenic fragment thereof. The composition may include an adjuvant. The at least one heterologous strain of *Clostridium difficile* may be strain VPI 10463. In another embodiment, the presently disclosed inventive concepts are directed to method for stimulating an immune response in a subject against *Clostridium difficile* by administering to said subject an amount of any of the above vaccine compositions sufficient to induce an immunogenic response in the subject wherein in at least one embodiment the immune response initiated by the vaccine composition is effective against the hypervirulent strain and at least one heterologous strain of *Clostridium difficile*, for example wherein the hypervirulent strain of *Clostridium difficile* is ribotype 027 and the at least one heterologous strain of *Clostridium difficile* is strain VPI 10463. The administration may be parenteral, subcutaneous, intramuscular, intraperitoneal or intravenous, for example.

While the presently disclosed inventive concepts have been described herein in connection with certain embodiments so that aspects thereof may be more fully understood and appreciated, it is not intended that the presently disclosed inventive concepts be limited to these particular embodiments. On the contrary, it is intended that all alternatives, modifications and equivalents are included within the scope of the presently disclosed inventive concepts as defined herein. Thus the examples described above, which include particular embodiments, will serve to illustrate the practice of the presently disclosed inventive concepts, it being understood that the particulars shown are by way of example and for purposes of illustrative discussion of particular embodiments of the presently disclosed inventive concepts only and are presented in the cause of providing what is believed to be the most useful and readily understood description of procedures as well as of the principles and conceptual aspects of the inventive concepts. Changes may be made in the formulation of the various compositions described herein, the methods described herein or in the steps or the sequence of steps of the methods described herein without departing from the spirit and scope of the presently disclosed inventive concepts.

What is claimed is:

1. A vaccine composition useful in initiating an immune response against *Clostridium difficile*, comprising: an immunogenic-effective amount of (a) the C-terminal domain of a toxin B derived from ribotype 027 hypervirulent strain of *Clostridium difficile*, consisting of amino acids 1651-2366 of SEQ ID NO: 1, (b) a pharmaceutically acceptable carrier, and further comprising (c) an adjuvant, wherein the immune response initiated by the vaccine composition is effective against the ribotype 027 strain from which it is derived and cross-neutralizing with respect to at least one heterologous strain of *Clostridium difficile* including strain VPI 10463.

2. The composition of claim 1, wherein the C-terminal domain is expressed from a recombinant source.

3. A method for stimulating an immune response in a subject against *Clostridium difficile* which comprises administering to said subject an amount of the vaccine composition of claim 1 sufficient to induce an immunogenic response in the subject.

4. The method of claim 3 wherein administration is parenteral, subcutaneous, intramuscular, intraperitoneal or intravenous.

* * * * *